(12) United States Patent
Wender et al.

(10) Patent No.: US 7,232,842 B2
(45) Date of Patent: Jun. 19, 2007

(54) KINASE INHIBITORS AND ASSOCIATED PHARMACEUTICAL COMPOSITIONS AND METHODS OF USE

(75) Inventors: Paul A. Wender, Menlo Park, CA (US); Marc J. Scanio, Glenview, IL (US)

(73) Assignee: Board of Trustees of the Leland Stanford Junior University, Stanford, CA (US)

( * ) Notice: Subject to any disclaimer, the term of this patent is extended or adjusted under 35 U.S.C. 154(b) by 194 days.

(21) Appl. No.: 10/754,433

(22) Filed: Jan. 9, 2004

(65) Prior Publication Data

US 2004/0142916 A1 Jul. 22, 2004

Related U.S. Application Data

(60) Provisional application No. 60/439,341, filed on Jan. 10, 2003.

(51) Int. Cl.
A61K 31/4035 (2006.01)
A61K 31/4045 (2006.01)
A61K 31/407 (2006.01)
C07D 487/00 (2006.01)
C07D 487/02 (2006.01)

(52) U.S. Cl. ............... 514/411; 514/410; 548/421; 548/429

(58) Field of Classification Search ........... 548/418, 548/518, 528, 546, 421, 429; 514/425, 410, 514/422, 411
See application file for complete search history.

(56) References Cited

U.S. PATENT DOCUMENTS

| 5,358,711 A | 10/1994 | May et al. |
| 5,521,184 A | 5/1996 | Zimmermann |
| 5,859,261 A | 1/1999 | Faul et al. |
| 6,117,861 A | 9/2000 | Engel et al. |
| 2002/0137789 A1 | 9/2002 | Wender et al. |
| 2002/0183364 A1 | 12/2002 | Tang |

FOREIGN PATENT DOCUMENTS

WO WO 02/30908 4/2002

OTHER PUBLICATIONS

Francis A. Carey, Advanced Organic Chemistry 3rd edition, p. 289-300.*
Bridges (2001), "Chemical Inhibitors of Protein Kinases," *Chem. Rev.* 101(8):2541-2571.
Carroll et al. (1997), "CGP 57148, a Tyrosine Kinase Inhibitor, Inhibits the Growth of Cells Expressing BCR-ABL, TEL-ABL, and TEL-PDGFR Fusion Proteins," *Blood* 90(12):4947-4952.
Dekker et al. (1994), "Protein Kinase C—A Question of Specificity," *Trends Biochem. Sci.* 19:73-77.
Engel et al. (2000), "Salt Form Selection and Characterization of LY333531 Mesylate Monohydrate," *International Journal of Pharmaceutics* 198(2):239-247.
Jacobson et al. (1996), "Role of Ced-3/ICE-Family Proteases in Staurosporine-Induced Programmed Cell Death," *The Journal of Cell Biology* 133(5):1041-1051.
Jirousek et al. (1996), "(S)-13-[(Dimethylamino)methyl]-10,11,14,15-tetrahydro-4,9:16,21-dimetheno-1H,13H-dibenzo[e,k]pyrrolo[3,4-h][1,4,13]oxadiazacyclohexadecene-1,3(2H)-dione (LY333531) and Related Analogues: Isozyme Selective Inhibitors of Protein Kinase Cβ," *J. Med. Chem.* 39(14):2664-2671.
Nishizuka (1992), "Intracellular Signaling by Hydrolysis of Phospholipids and Activation of Protein Kinase C," *Science* 258:607-614.
Takai et al. (1977), "Studies on a Cyclic Nucleotide-Independent Protein Kinase and Its Proenzyme in Mammalian Tissues," *The Journal of Biological Chemistry* 252(21):7603-7609.
Tamaoki et al. (1986), "Staurosporine, A Potent Inhibitor of Phospholipid/Ca++Dependent Protein Kinase," *Biochemical and Biophysical Research Communications* 135(2):397-402.

(Continued)

Primary Examiner—Joseph K. McKane
Assistant Examiner—Yong Chu
(74) Attorney, Agent, or Firm—Mintz, Levin, Cohn, Ferris, Glovsky and Popeo, P.C.; Dianne E. Reed; Isaac M. Rutenberg

(57) ABSTRACT

The invention provides novel compounds useful as kinase inhibitors or as starting materials And/or intermediates in the synthesis of compounds useful as kinase inhibitors. The compounds have The general structure of formula (I)

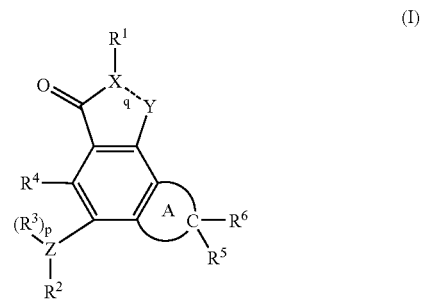

wherein A is a 3- to 8-membered ring, optionally substituted and/or heteroatom-containing, and $R^1$, $R^2$, $R^3$, $R^4$, $R^5$, $R^6$, X, Y, Z, p, and q are as defined herein. The compounds may also be in the form of a salt, ester, amide, or other analog. In preferred compounds, A is a 5- to 8-membered ring, $R^1$ is hydrogen, q is a bond, X is N, Y is C=O, Z is N, $R^2$ contains a terminal amino moiety, p is 1, and $R^3$ and $R^4$ are linked to form a pyrrole ring fused to a second cyclic group. Pharmaceutical compositions and methods for using the compounds are also provided.

19 Claims, No Drawings

OTHER PUBLICATIONS

Wender et al. (1988), "Modeling of the Bryostatins to the Phorbol Ester Pharmacophore on Protein Kinase C," *Proc. Natl. Acad. Sci. USA 85*:7197-7201.

Wender et al. (1986), "Analysis of the Phorbol Ester Pharmacophore on Protein Kinase C as a Guide to the Rational Design of New Classes of Analogs," *Proc. Natl. Acad. Sci. USA 83*:4214-4218.

Wender et al. (1998), "The Chemistry-Medicine Continuum: Synthetic, Computer, Spectroscopic and Biological Studies on New Chemotherapeutic Leads," *Pure & Appl. Chem. 70*(3):539-546.

Wender et al. (1998), "Synthesis of the First Members of a New Class of Biologically Active Bryostatin Analogues," *J. Am. Chem. Soc. 120*(18):4534-4535.

Zimmerman et al. (1997), "Potent and Selective Inhibitors of the ABL-Kinase: Phenylamino-Pyrimidine (PAP) Derivatives," *Bioorganic & Medicinal Chemistry Letters 7*(2):187-192.

Schore, "Transition-Metal-Mediated Cycloaddition Reactions of Alkynes in Organic Synthesis," *Chem. Rev.*, 1988, 88, 1081-1119.

\* cited by examiner

KINASE INHIBITORS AND ASSOCIATED PHARMACEUTICAL COMPOSITIONS AND METHODS OF USE

CROSS-REFERENCE TO RELATED APPLICATIONS

This application claims priority under 35 U.S.C. §119(e)(1) to provisional U.S. App. Ser. No. 60/439,341, filed Jan. 10, 2003, the disclosure of which is incorporated by reference herein.

GOVERNMENT RIGHTS

This invention was made with United States Government support under grant number NIH CA31845 awarded by National Institutes of Health. The United States Government has certain rights in this invention.

TECHNICAL FIELD

This invention relates generally to kinase inhibitors, and more particularly relates to novel isoindolone analogs that are inhibitors of protein kinases, particularly tyrosine kinases and serine-threonine kinases. The invention also pertains to pharmaceutical compositions and methods for treating conditions, diseases and disorders that are responsive to administration of a protein kinase inhibitor. Such indications include cancer, atherosclerosis, diabetes, disorders of the central nervous system (CNS), and autoimmune diseases such as rheumatoid arthritis.

BACKGROUND

It has long been established that proteins are reversibly modified in response to many extracellular and intracellular stimuli. One such mechanism is the phosphorylation of proteins by ATP, wherein a phosphate group is added to the hydroxyl group-bearing side chain of serine, threonine, or tyrosine residues. This reaction is catalyzed by enzymes known as protein kinases, which transfer the γ-phosphate group from ATP to the side-chain hydroxyl groups of substrate proteins. The reaction is reversible in a hydrolysis reaction catalyzed in situ by phosphatase enzymes. These phosphorylation and hydrolysis reactions have been established as critical to intracellular signaling processes, regulation of cellular functions, and activation or deactivation of cellular processes.

In mammals, protein kinases tend to fall within three groups: the serine-threonine kinases (S/TKs); the tyrosine kinases (TKs); and the relatively dual function kinases that act as both S/TKs and TKs. TKs have been identified as associated with cell proliferation, activation, or differentiation, and excessive TK activity has been observed in many disease states including benign and malignant proliferative disorders and immune system disorders. Certain TKs have also been identified as mediators of angiogenesis and therefore involved in the progression of cancer and other diseases involving inappropriate vascularization. For example, it has been found that chronic niyelogenous leukemia (CML) is a result of a chromosomal abnormality resulting in production of an a typical TK in the form of a BCR-ABL fusion protein. Inhibitors targeting that fusion protein have been made, and one such inhibitor, imatinib mesylate (the mesylate salt of 4-[(4-methyl-1-piperazinyl)methyl]-N-[4-methyl-3-[[4-(3-pyridinyl)-2-pyrinmidinyl]amino]-phenyl]benzamide), is now commercially available under the tradename Gleevec. See, e.g., Carroll et al. (1997) *Blood* 90:4947, Zimmerman et al. (1997) *Bioorg. Med. Chem. Lett.* 7:187, Bridges (2001) *Chem. Rev.* 101:2541, and U.S. Pat. No. 5,521,184 to Zimmerman.

A representative and important family of S/TK kinases are known as "protein kinase C" (PKC), which was identified in 1977 (Takai et al. (1977) *J. Biol. Chem.* 252:7603). PKC has 12 isoforms that fall into three groups, the conventional or c-PKCs, activated by diacylglycerol and calcium, the novel or n-PKCs, which do not require calcium for activation, and the a typical or a-PKCs, which require neither calcium nor diacylglycerol for activation. See Bridges (2001), supra, Nishizuka (1992) *Science* 258:607, and Dekker et al. (1994) *Trends Biochem. Sci.* 19:73. PKC and its various isoforms have been associated with a variety of disorders and diseases, including cancer, CNS disorders, Alzheimer's disease, cardiovascular disease, dermatological disorders, inflammation, autoimmune diseases such as rheumatoid arthritis, and diabetic complications.

Staurosporin, an indolocarbazole natural product, was identified as the first potent inhibitor of PKC, exhibiting an $IC_{50}$ value of 2.7 nM. Tamaoki et al. (1986) *Biochem. Biophys. Res. Commun.* 135:397. Staurosporin is known to induce programmed cell death and has been used in conjunction with other anti-cancer drugs. Jacobson et al. (1996) *J. Cell Biol.* 133:1041.

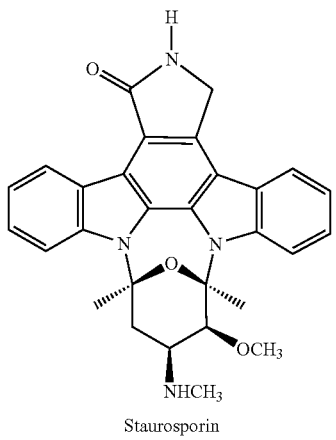

Staurosporin

While exhibiting inhibition in the low-nanomolar range, however, staurosporin inhibits five of the PKC isoforms with an $IC_{50}$ below 10 nM, and inhibits many other kinases as well. The compound is not, therefore, useful as a selective PKC inhibitor.

Several additional inhibitors of PKC have been investigated for their inhibitory activity on the proliferation of several tumor cell lines. For example, the phorbol ester and bryostatins are known to bind and regulate PKC competitively with diacylglycerol. See, e.g., Wender et al. (1988) *Proc. Natl. Acad. Sci. USA* 85:7197, Wender et al. (1986) *Proc. Natl. Acad. Sci. USA* 83:4214, Wender et al. (1998) *Pure Appl. Chem.* 70:539, and Wender et al. (1998) *J. Am. Chem. Soc.* 120:4534. Bryostatin 1, for example, has been established as a potent activator of the c-PKCs.

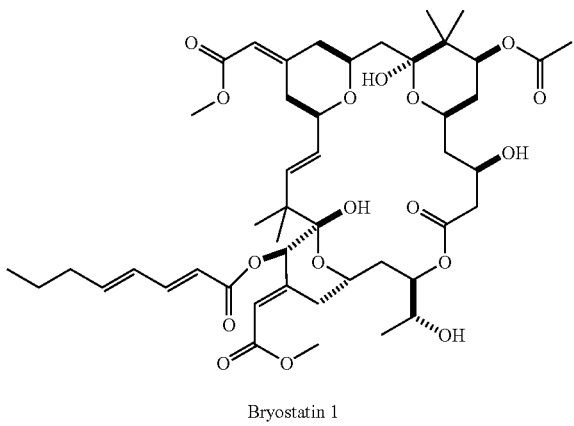

Bryostatin 1

Although the bryostatins have been known for some time, their low natural abundance, difficulty in isolation, and severely limited availability through total synthesis have impeded efforts to advance their clinical development. Chemically synthesized simplified analogues of the bryostatins have been disclosed, however, and have exhibited PKC inhibitory activity; see U.S. Patent Application Publication No. 2002/0137789 A1 to Wender et al.

Other classes of compounds known to bind to and regulate PKC are indolo[2,3-α]carbazoles and bisindolylmaleimides.

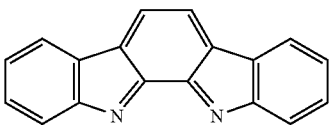

indolo[2,3-α]carbazole

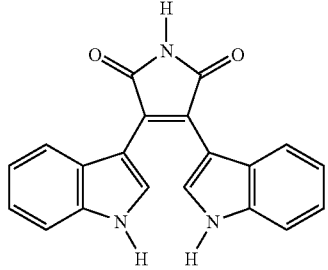

bisindolylmaleimide

One recently developed bisindolylmaleimide, LY 333531, has been established as particularly selective for the β isoforms of PKC:

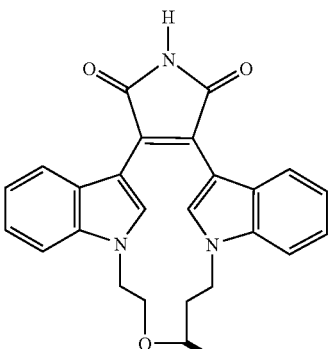

LY 333531

See Engel et al. (2000) *Intl. J. Pharmaceutics* 198(2):239, Jirousec et al. (1996) *J. Med. Chem.* 39(14):2664, U.S. Pat. No. 5,859,261 to Faul et al., and U.S. Pat. No. 6,117,861 to Engel et al.

While a number of kinase inhibitors have, accordingly, been studied and developed, there is an ongoing need for potent inhibitors that can be readily modified so as to achieve selectivity with respect to a particular kinase, and that can be readily synthesized from relatively simple starting materials. Optimal kinase inhibitors would also be quite potent while exhibiting very low toxicity.

The present invention is the result of extensive, systematic research in the design of novel kinase inhibitors in the form of isoindolone analogs, particularly analogs that derive from the use of staurosporin as a pharmacophoric template. To the best of applicants' knowledge, the compounds, compositions, and methods of the invention are completely unknown and completely unsuggested by the art.

SUMMARY OF THE INVENTION

The present invention is directed to the aforementioned need in the art, and provides novel compounds that act as kinase inhibitors, and/or that serve as useful starting materials and/or intermediates in the synthesis of a kinase inhibitor. The novel compounds, analogs of isoindolone, display considerable advantages relative to known kinase inhibitors. For example, many of the present compounds are potent kinase inhibitors, exhibit low $IC_{50}$ values, are readily synthesized from simple starting materials using straightforward synthetic chemistry, and can be modified so as to provide selectivity with respect to inhibition of a particular kinase.

In one aspect of the invention, then, a compound is provided in the form of an isoindolone analog having the structure of formula (I)

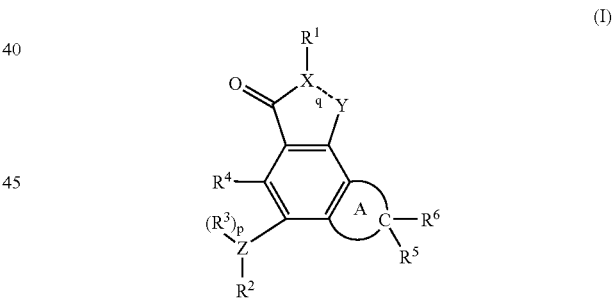

wherein:

A is a 3- to 8-membered ring, optionally substituted and/or heteroatom-containing;

$R^1$ is H or lower alkyl;

$R^2$ is H, a heteroatom-protecting group, or $-L-NR^7R^8$ wherein L is a linker containing 1 to 6 spacer atoms, and $R^7$ and $R^8$ are independently selected from hydrogen, nitrogen-protecting groups, $C_1-C_{24}$ hydrocarbyl, substituted $C_1-C_{24}$ hydrocarbyl, heteroatom-containing $C_1-C_{24}$ hydrocarbyl, and substituted heteroatom-containing $C_1-C_{24}$ hydrocarbyl;

$R^3$ and $R^4$ are independently selected from hydrogen, $C_1-C_{24}$ hydrocarbyl, substituted $C_1-C_{24}$ hydrocarbyl, heteroatom-containing $C_1-C_{24}$ hydrocarbyl, and substituted heteroatom-containing $C_1-C_{24}$ hydrocarbyl, or $R^3$ and $R^4$ taken together form a heterocyclic ring optionally fused to an additional cyclic group;

$R^5$ is a substituent selected from hydrogen, $C_1$–$C_{24}$ hydrocarbyl, substituted $C_1$–$C_{24}$ hydrocarbyl, heteroatom-containing $C_1$–$C_{24}$ hydrocarbyl, or substituted heteroatom-containing $C_1$–$C_{24}$ hydrocarbyl;

$R^6$ is a substituent selected from hydrogen, halo, hydroxyl, sulfhydryl, $C_1$–$C_{24}$ alkoxy, $C_2$–$C_{24}$ alkenyloxy, $C_2$–$C_{24}$ alkynyloxy, $C_5$–$C_{24}$ aryloxy, $C_2$–$C_{24}$ alkylcarbonyl, $C_6$–$C_{24}$ arylcarbonyl, $C_2$–$C_{24}$ alkylcarbonyloxy, $C_6$–$C_{24}$ arylcarbonyloxy, halocarbonyl, $C_2$–$C_{24}$ alkylcarbonato, $C_6$–$C_{24}$ arylcarbonato, carboxy, carboxylato, carbamoyl, mono-($C_1$–$C_{24}$ alkyl)-substituted carbamoyl, di-($C_1$–$C_{24}$ alkyl)-substituted carbamoyl, mono-($C_6$–$C_{24}$ aryl)-substituted carbamoyl, mono-($C_6$–$C_{24}$ aryl)-substituted carbamoyl, di-N-($C_1$–$C_{24}$ alkyl), N-($C_6$–$C_{24}$ aryl)-substituted carbamoyl, thiocarbamoyl, carbamido, cyano, isocyano, cyanato, isocyanato, isothiocyanato, azido, formyl, thioformyl, amino, mono-($C_1$–$C_{24}$ alkyl)-substituted amino, di-($C_1$–$C_{24}$ alkyl)-substituted amino, mono-($C_5$–$C_{24}$ aryl)-substituted amino, di-($C_5$–$C_{24}$aryl)-substituted amino, di-N-($C_1$–$C_{24}$ alkyl), N-($C_6$–$C_{24}$ aryl)-substituted amino, $C_2$–$C_{24}$ alkylamido, $C_6$–$C_{24}$ arylamido, imino, alkylimino, arylimino, nitro, nitroso, sulfo, sulfonato, $C_1$–$C_{24}$ alkylthio, $C_5$–$C_{24}$ arylthio, $C_1$–$C_{24}$ alkylsulfinyl, $C_5$–$C_{24}$ arylsulfinyl, $C_1$–$C_{24}$ alkylsulfonyl, $C_5$–$C_{24}$ arylsulfonyl, phosphono, phosphonato, phosphinato, phosphono, phosphino, $C_1$–$C_{24}$ alkyl, $C_2$–$C_{24}$ alkenyl, $C_2$–$C_{24}$ alkynyl, $C_5$–$C_{24}$ aryl, $C_6$–$C_{24}$ alkaryl, and $C_6$–$C_{24}$ aralkyl, wherein any of the foregoing substituents, if the substituent permits, may be further substituted, or wherein $R^5$ and $R^6$ taken together form =O, =S, or =$NR^9$ where $R^9$ is selected from hydrogen, $C_1$–$C_{24}$ hydrocarbyl, substituted $C_1$–$C_{24}$ hydrocarbyl, heteroatom-containing $C_1$–$C_{24}$ hydrocarbyl, and substituted heteroatom-containing $C_1$–$C_{24}$ hydrocarbyl;

X is N, $NR^{10}$, P, $PR^{16}$, O, or S, wherein $R^{15}$ and $R^{16}$ are selected from hydrogen, $C_1$–$C_{24}$ hydrocarbyl, substituted $C_1$–$C_{24}$ hydrocarbyl, heteroatom-containing $C_1$–$C_{24}$ hydrocarbyl, and substituted heteroatom-containing $C_1$–$C_{24}$ hydrocarbyl;

Y is selected from $CR^{12}R^{13}$ and $CR^{12}R^{13}H$ in which $R^{12}$ is defined as for $R^5$, and $R^{13}$ is defined as for $R^6$, and wherein $R^{12}$ and $R^{13}$ may be taken together to form =O, =S, or =N$R^{14}$ where $R^{14}$ is defined as for $R^9$;

Z is N, $NR^{15}$, P, $PR^{16}$, O, or S, wherein $R^{15}$ and $R^{16}$ are selected from hydrogen, $C_1$–$C_{24}$ hydrocarbyl, substituted $C_1$–$C_{24}$ hydrocarbyl, heteroatom-containing $C_1$–$C_{24}$ hydrocarbyl, and substituted heteroatom-containing $C_1$–$C_{24}$ hydrocarbyl;

p is zero or 1, with the proviso that when p is zero, then Z is $NR^{15}$, $PR^{16}$, O, or S, and when p is 1, then Z is N or P; and q is an optional covalent bond between X and Y, with the proviso that when q is absent, then X is $NR^{10}$, $PR^{11}$, O, or S, and Y is $CR^{12}R^{13}H$, and when q is present, then X is N or P, and Y is $CR^{12}R^{13}$.

In another embodiment, the invention encompasses pharmaceutical compositions containing a therapeutically effective amount of a novel compound as provided herein in combination with a pharmaceutically acceptable carrier. The compositions are generally "unit dosage" forms in which the therapeutically effective amount is suitable for a single dosage. The compositions may be immediate release or controlled release, and, if controlled release, are preferably sustained release. For those compounds that are orally active, oral dosage forms are preferred, in which case the carrier is one that is suitable for oral ingestion.

The invention also provides a method for treating a condition, disease, or disorder in a mammalian patient by administering a therapeutically effective amount of a kinase inhibitor as provided herein. Generally, the inhibitor is administered in a pharmaceutical composition as described above.

DETAILED DESCRIPTION OF THE PREFERRED EMBODIMENTS

Definitions and Nomenclature

Unless otherwise indicated, the invention is not limited to specific synthetic methods, analogs, substituents, pharmaceutical formulations, formulation components, modes of administration, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a substituent" includes a single substituent as well as two or more substituents that may be the same or different, reference to "a compound" encompasses a combination or mixture of different compounds as well as a single compound, reference to "a pharmaceutically acceptable carrier" includes two or more such carriers as well as a single carrier, and the like. In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Preferred lower alkyl substituents contain 1 to 3 carbon atoms, and particularly preferred such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, preferably 2 to 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, preferably 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred lower alkoxy substituents contain 1 to 3 carbon atoms, and particularly preferred such substituents contain 1 or 2 carbon atoms (i.e., methoxy and ethoxy). The terms "alkenyloxy" and "alkynyloxy" are defined in an analogous manner.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7–Cyclooctyinaphthyl, 3-ethyl-cyclopenta-1,4-diene, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl", and "aralkyl" are as defined above.

The term "cyclic" refers to alicyclic or aromatic substituents that may or may not be substituted and/or heteroatom containing, and that may be monocyclic, bicyclic, or polycyclic.

The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" are used in the conventional sense to refer to a chloro, bromo, and fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur, preferably nitrogen or oxygen. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene et al., *Protective Groups in Organic Synthesis* (New York: Wiley, 1991).

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$–$C_{24}$ alkoxy, $C_2$–$C_{24}$ alkenyloxy, $C_2$–$C_{24}$ alkynyloxy, $C_5$–$C_{24}$ aryloxy, acyl (including $C_2$–$C_{24}$ alkylcarbonyl (—CO-alkyl) and $C_6$–$C_{24}$ arylcarbonyl (—CO-aryl)), acyloxy (—O-acyl), $C_2$–$C_{24}$ alkoxycarbonyl (—(CO)—O-alkyl), $C_6$–$C_{24}$ aryloxycarbonyl (—(CO)—O-aryl), halocarbonyl (—CO)—X where X is halo), $C_2$–$C_{24}$ alkylcarbonato (—O—(CO)—O-alkyl), $C_6$–$C_{24}$ arylcarbonato (—O—(CO)—O-aryl), carboxy (—COOH), carboxylato (—COO—), carbamoyl (—(CO)—NH$_2$), mono-($C_1$–$C_{24}$ alkyl)-substituted carbamoyl (—(CO)—NH($C_1$–$C_{24}$ alkyl)), di-($C_1$–$C_{24}$ alkyl)-substituted carbamoyl (—(CO)—N($C_1$–$C_{24}$ alkyl)$_2$), mono-($C_6$–$C_{24}$ aryl)-substituted carbamoyl (—(CO)—NH-aryl), di-($C_6$–$C_{24}$ aryl)-substituted carbamoyl (—(CO)—N(aryl)$_2$), di-N-($C_1$–$C_{24}$ alkyl), N-($C_6$–$C_{24}$ aryl)-substituted carbamoyl, thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono-($C_1$–$C_{24}$ alkyl)-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, $C_2$–$C_{24}$ alkylamido (—NH—(CO)-alkyl), $C_6$–$C_{24}$ arylamido (—NH—(CO)-aryl), imino (—CR=NH where R=hydrogen, $C_1$–$C_{24}$ alkyl, $C_5$–$C_{24}$ aryl, $C_6$–$C_{24}$ alkaryl, $C_6$–$C_{24}$ aralkyl, etc.), alkylimino (—CR=N(alkyl), where R=hydrogen, $C_1$–$C_{24}$ alkyl, $C_5$–$C_{24}$ aryl, $C_6$–$C_{24}$ alkaryl, $C_6$–$C_{24}$ aralkyl, etc.), arylimino (—CR=N(aryl), where R=hydrogen, $C_1$–$C_{24}$ alkyl, $C_5$–$C_{24}$aryl, $C_6$–$C_{24}$ alkaryl, $C_6$–$C_{24}$ aralkyl, etc.), nitro (—NO$_2$), nitroso (—NO), sulfo (—SO$_2$—OH), sulfonato (—SO$_2$—O—), $C_1$–$C_{24}$ alkylsulfanyl (—S-alkyl; also termed "alkylthio"), arylsulfanyl (—S-aryl; also termed "arylthio"), $C_1$–$C_{24}$ alkylsulfinyl (—(SO)-alkyl), $C_5$–$C_{24}$ arylsulfinyl (—(SO)-aryl), $C^1$–$C_{24}$ alkylsulfonyl (—SO$_2$-alkyl), $C_5$–$C_{24}$ arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$); and the hydrocarbyl moieties $C_1$–$C_{24}$ alkyl (preferably $C^2$–$C_{18}$ alkyl, more preferably $C_1$–$C_{12}$ alkyl, most preferably $C_1$–$C_6$ alkyl), $C_2$–$C_{24}$ alkenyl (preferably $C_2$–$C_{18}$ alkenyl, more preferably $C_2$–$C_{12}$ alkenyl, most preferably $C_2$–$C_6$ alkenyl), $C_2$–$C_{24}$ alkynyl (preferably $C_2$–$C_{18}$ alkynyl, more preferably $C_2$–$C_{12}$ alkynyl, most preferably $C_2$–$C_6$ alkynyl), $C_5$–$C_{24}$ aryl (preferably $C_5$–$C_{14}$ aryl), $C_6$–$C_{24}$ alkaryl (preferably $C_6$–$C_{18}$ alkaryl), and $C_6$–$C_{24}$ aralkyl (preferably $C_6$–$C_{18}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase an "optionally present" bond as indicated by a dotted line - - - in the chemical formulae herein means that a bond may or may not be present.

When referring to a compound of the invention as an active agent, applicants intend the term "compound" or "active agent" to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, "treating" a patient with a compound of the invention includes prevention of a particular disorder or adverse physiological event in a susceptible individual as well as treatment of a clinically symptomatic individual by inhibiting or causing regression of a disorder or disease. For example, treatment of cancer encompasses chemoprevention in a patient susceptible to developing cancer (e.g., at a higher risk, as a result of genetic predisposition, environmental factors, or the like) and/or in cancer survivors at risk of cancer recurrence, as well as treatment of a cancer patient dual by inhibiting or causing regression of a disorder or disease.

By the terms "effective amount" and "therapeutically effective amount" of a compound of the invention is meant a nontoxic but sufficient amount of the drug or agent to provide the desired effect.

The term "dosage form" denotes any form of a pharmaceutical composition that contains an amount of active agent sufficient to achieve a therapeutic effect with a single administration. When the formulation is a tablet or capsule, the dosage form is usually one such tablet or capsule. The frequency of administration that will provide the most effective results in an efficient manner without overdosing will vary with the characteristics of the particular active agent, including both its pharmacological characteristics and its physical characteristics, such as hydrophilicity.

The term "controlled release" refers to a drug-containing formulation or fraction thereof in which release of the drug is not immediate, i.e., with a "controlled release" formulation, administration does not result in immediate release of the drug into an absorption pool. The term is used interchangeably with "nonimmediate release" as defined in *Remington: The Science and Practice of Pharmacy, Nineteenth Ed.* (Easton, Pa.: Mack Publishing Company, 1995). In general, the term "controlled release" as used herein includes sustained release and delayed release formulations.

The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

II. Compounds of the Invention and Synthesis Thereof

The present invention provides new compounds useful as kinase inhibitors, wherein the compounds have the structure of formula (I)

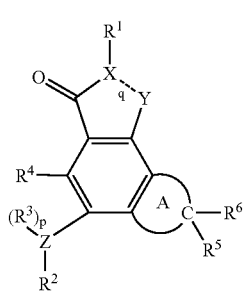

(I)

wherein the various substituents are as defined earlier herein. More specifically:

A is a 3- to 8-membered ring, preferably a 5- to 8-membered ring, is optionally substituted and/or heteroatom-containing, and may or may not be aromatic. Examples of preferred A rings thus include, but are not limited to, cyclopropenyl, cyclobutenyl, cyclopentenyl, cyclohexenyl, cyclohexadienyl, cyclooctenyl, cyclooctadienyl, cyclooctatrienyl (taking the double bond shared with the adjacent fused phenyl group into account), any of which may be substituted with one or more nonhydrogen substituents (e.g., halo, hydroxy, alkoxy, etc.) and/or contain substituted or unsubstituted heteroatoms (e.g., N, NR where R represents a substituent, O, S, etc.).

$R^1$ is hydrogen or lower alkyl, preferably hydrogen or methyl, most preferably hydrogen.

$R^2$ is H, a heteroatom-protecting group, or -L-NR$^7$R$^8$ wherein L is a linker containing 1 to 6 spacer atoms, and $R^7$ and $R^8$ are independently selected from hydrogen, nitrogen-protecting groups, $C_1$–$C_{24}$ hydrocarbyl, substituted $C_1$–$C_{24}$ hydrocarbyl, heteroatom-containing $C_1$–$C_{24}$ hydrocarbyl, and substituted heteroatom-containing $C_1$–$C_{24}$ hydrocarbyl. When $R^2$ is a heteroatom-protecting group, protecting the heteroatom "Z" as defined infra, the protecting group is selected according to the particular heteroatom and the reaction or conditions under which protection is required. When Z is a nitrogen atom, suitable protecting groups are nitrogen-protecting groups such as formyl, trityl, phthalimido, trichloroacetyl, t-butoxy-carbonyl ("Boc" or "t-Boc"), 2-(trimethylsilyl)ethoxymethyl (SEM), and the like. Protecting groups for numerous functional groups and heteroatoms are described in Greene et al., supra.

$R^3$ and $R^4$ are independently selected from hydrogen, hydrocarbyl (e.g., $C_1$–$C_{24}$ alkyl, $C_2$–$C_{24}$ alkenyl, $C_2$–$C_{24}$ alkynyl, $C_5$–$C_{24}$ aryl, $C_6$–$C_{24}$ alkaryl, or $C_6$–$C_{24}$ aralkyl), substituted hydrocarbyl (e.g., substituted $C_1$–$C_{24}$ alkyl, $C_2$–$C_{24}$ alkenyl, $C_2$–$C_{24}$ alkynyl, $C_5$–$C_{24}$ aryl, $C_6$–$C_{24}$ alkaryl, or $C_6$–$C_{24}$ aralkyl), heteroatom-containing hydrocarbyl (e.g., $C_1$–$C_{24}$ heteroalkyl, $C_3$–$C_{24}$ heteroaryl, heteroatom-containing $C_4$–$C_{24}$ aralkyl, or heteroatom-containing $C_4$–$C_{24}$ alkaryl), or substituted heteroatom-containing hydrocarbyl (e.g., substituted $C_1$–$C_{24}$ heteroalkyl, $C_3$–$C_{24}$ heteroaryl, heteroatom-containing $C_6$–$C_{24}$ aralkyl, or heteroatom-containing $C_6$–$C_{24}$ alkaryl), or $R^3$ and $R^4$ taken together form a heterocyclic ring, generally a 5–8 membered ring, preferably a 5-membered ring (e.g., pyrrole) optionally fused to an additional cyclic group, e.g., a monocyclic 5- or 6-membered aromatic ring that may be substituted and/or heteroatom-containing (e.g., phenyl, substituted phenyl, pyridyl, N-substituted pyridyl, C-substituted pyridyl, etc.).

$R^5$ is a substituent selected from hydrogen, $C_1$–$C_{24}$ hydrocarbyl, substituted $C_1$–$C_{24}$ hydrocarbyl, heteroatom-containing $C_1$–$C_{24}$ hydrocarbyl, or substituted heteroatom-containing $C_1$–$C_{24}$ hydrocarbyl, and $R^6$ is a substituent selected from hydrogen, halo, hydroxyl, sulfhydryl, $C_1$–$C_{24}$ alkoxy, $C_2$–$C_{24}$ alkenyloxy, $C_2$–$C_{24}$ alkynyloxy, $C_5$–$C_{24}$ aryloxy, $C_2$–$C_{24}$ alkylcarbonyl, $C_6$–$C_{24}$ arylcarbonyl, $C_2$–$C_{24}$ alkylcarbonyloxy, $C_6$–$C_{24}$ arylcarbonyloxy, halocarbonyl, $C_2$–$C_{24}$ alkylcarbonato, $C_6$–$C_{24}$ arylcarbonato, carboxy, carboxylato, carbamoyl, mono-($C_1$–$C_{24}$ alkyl)-substituted carbamoyl, di-($C_1$–$C_{24}$ alkyl)-substituted carbamoyl, mono-($C_6$–$C_{24}$ aryl)-substituted carbamoyl, thiocarbamoyl, carbamido, cyano, isocyano, cyanato, isocyanato, isothiocyanato, azido, formyl, thioformyl, amino, mono-($C_1$–$C_{24}$alkyl)-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, $C_2$–$C_{24}$ alkylamido, $C_6$–$C_{24}$ arylamido, imino, alkylimino, arylimino, nitro, nitroso, sulfo, sulfonato, $C_1$–$C_{24}$ alkylthio, $C_5$–$C_{24}$ arylthio, $C_1$–$C_{24}$ alkylsulfinyl, $C_5$–$C_{24}$ arylsulfinyl, $C_1$–$C_{24}$ alkylsulfonyl, $C_5$–$C_{24}$ arylsulfonyl, phosphono, phosphonato, phosphinato, phosphono, phosphino, $C_1$–$C_{24}$ alkyl, $C_2$–$C_{24}$ alkenyl, $C_2$–$C_{24}$ alkynyl, $C_5$–$C_{24}$ aryl, $C_6$–$C_{24}$ alkaryl, and $C_6$–$C_{24}$ aralkyl, wherein any of the foregoing substituents, if the substituent permits, may be further substituted, or $R^5$ and $R^6$ taken together form =O, =S, or =NR$^9$ where $R^9$ is selected from hydrogen, $C_1$–$C_{24}$ hydrocarbyl, substituted $C_1$–$C_{24}$ hydrocarbyl, heteroatom-containing $C_1$–$C_{24}$ hydrocarbyl, and substituted heteroatom-containing $C_1$–$C_{24}$ hydrocarbyl.

X is N, NR$^{10}$, P, PR$^{11}$, O, or S, wherein R$^{10}$ and R$^{11}$ are selected from hydrogen, $C_1$–$C_{24}$ hydrocarbyl, substituted $C_1$–$C_{24}$ hydrocarbyl, heteroatom-containing $C_1$–$C_{24}$ hydrocarbyl, and substituted heteroatom-containing $C_1$–$C_{24}$ hydrocarbyl, preferably from hydrogen, $C^1$–$C_{12}$ hydrocarbyl, substituted $C^1$–$C_{12}$ hydrocarbyl, heteroatom-containing $C^1$–$C_{12}$ hydrocarbyl, and substituted heteroatom-containing $C^1$–$C_{12}$ hydrocarbyl.

Y is selected from CR$^{12}$R$^{13}$ and CR$^{12}$R$^{13}$H in which R$^{12}$ is defined as for R$^5$, and R$^{13}$ is defined as for R$^6$, and wherein $R^{12}$ and $R^{13}$ may be taken together to form =O, =S, or =NR$^{14}$ where R$^{14}$ is defined a for R$^9$.

The bond q indicated by " - - - " is an optional covalent bond between X and Y. Accordingly, when q is absent, then X is NR$^{10}$, PR$^{11}$, O, or S, and Y is CR$^{12}$R$^{13}$H, and when q is present, then X is N or P, and Y is CR$^{12}$R$^{13}$. Preferably, q is present, X is N, and Y is CR$^{12}$R$^{13}$ wherein R$^{12}$ and R$^{13}$ taken together form =O.

Z is N, NR$^{15}$, P, PR$^{16}$, O, or S, wherein R$^{15}$ and R$^{16}$ are selected from hydrogen, $C_1$–$C_{24}$ hydrocarbyl, substituted $C_1$–$C_{24}$ hydrocarbyl, heteroatom-containing $C_1$–$C_{24}$ hydrocarbyl, and substituted heteroatom-containing $C_1$–$C_{24}$ hydrocarbyl, preferably from hydrogen, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl.

The subscript p is zero or 1, meaning that the substituent R$^3$ may or may not be present. It will be appreciated that when p is zero, then Z is NR$^{15}$, PR$^{16}$, O, or S, and when p is 1, then Z is N or P. Preferably, p is 1.

Accordingly, in a representative preferred embodiment of the invention, then:

A is a 5- to 8-membered ring, optionally substituted and/or heteroatom-containing;
R$^1$ is H;
p is 1;
q is present;
X is N;
Y is CR$^{12}$R$^{13}$ in which R$^{12}$ and R$^{13}$ taken together form =O; and
Z is N, such that the compound has the structure of formula (II)

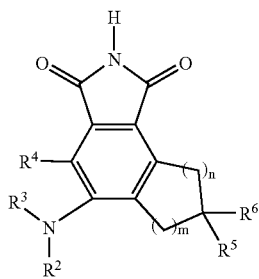

(II)

in which m is zero 1, 2, 3, 4, or 5, n is zero, 1, 2, 3, 4, or 5, and the sum of m and n is in the range of 2 to 5 inclusive.

Within the structure of formula (II), more preferred compounds are those wherein:

R$^2$ is -L-NR$^7$R$^8$ wherein L is hydrocarbylene containing 2 to 6 spacer atoms, and R$^7$ and R$^8$ are independently selected from hydrogen, nitrogen-protecting groups, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl;

R$^3$ and R$^4$ are independently selected from hydrogen, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl, or R$^3$ and R$^4$ taken together form a five-membered N-heterocyclic ring, preferably a pyridine ring, fused to an additional cyclic group, preferably a 5–8 membered ring that may or may not be heterocyclic and/or substituted;

R$^5$ is selected from hydrogen and lower alkyl, and R$^6$ is a substituent selected from hydrogen, halo, hydroxyl, sulfhydryl, $C_1$–$C_{12}$ alkoxy, $C_5$–$C_{14}$ aryloxy, $C_2$–$C_{12}$ alkylcarbonyloxy, $C_6$–$C_{14}$ arylcarbonyloxy, halocarbonyl, $C_2$–$C_{12}$ alkylcarbonato, $C_6$–$C_{14}$ arylcarbonato, carboxy, carboxylato, carbamoyl, mono-($C_1$–$C_{12}$ alkyl)-substituted carbamoyl, di-($C_1$–$C_{12}$ alkyl)-substituted carbamoyl, mono-($C_6$–$C_{14}$ aryl)-substituted carbamoyl, thiocarbamoyl, carbamido, cyano, isocyano, formyl, thioformyl, amino, mono-($C_1$–$C_{12}$ alkyl)-substituted amino, di-($C_1$–$C_{12}$ alkyl)-substituted amino, mono-($C_5$–$C_{14}$aryl)-substituted amino, di-($C_5$–$C_{14}$aryl)-substituted amino, $C_2$–$C_{14}$ alkylamido, $C_6$–$C_{14}$ arylamido, $C_1$–$C_{12}$ alkylthio, $C_5$–$C_{14}$ arylthio, $C_1$–$C_{12}$ alkyl, $C_2$–$C_{12}$ alkenyl, $C_5$–$C_{14}$aryl, $C_6$–$C_{16}$ alkaryl, and $C_6$–$C_{16}$ aralkyl, wherein any of the foregoing substituents, if the substituent permits, may be further substituted, or wherein R$^5$ and R$^6$ taken together form =O, =S, or =NR$^9$ where R$^9$ is selected from $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl.

Accordingly, the more preferred compounds herein have the structure of formula (III)

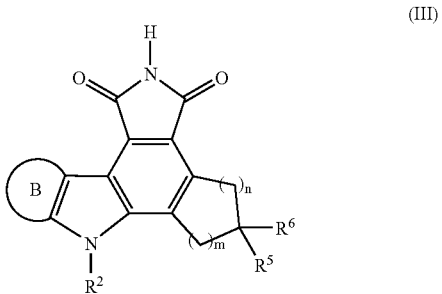

(III)

wherein B is a 5- to 8-membered ring, optionally substituted and/or heteroatom-containing. In a still more preferred embodiment: B is a 5- or 6-membered aryl, substituted aryl, heteroaryl, or substituted heteroaryl ring, e.g., phenyl or phenyl substituted with up to 4 nonhydrogen substituents; the sum of m and n is 2, 3, or 4; R$^5$ is hydrogen and R$^6$ is selected from hydroxyl, sulfhydryl, lower alkoxy, and lower alkylthio, or R$^5$ and R$^6$ together form =O; L is $C_2$–$C_4$ alkylene; and R$^7$ and R$^8$ are independently selected from hydrogen, lower alkyl, and nitrogen-protecting groups. Such compounds have the structure of formula (IV)

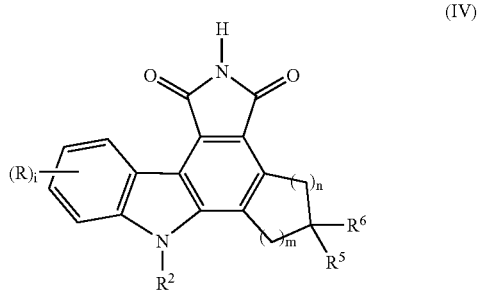

(IV)

in which i is an integer in the range of zero to 4, and each R is a nonhydrogen substituent.

Specific such compounds exemplified herein include those wherein i is zero, m is 2, n is 2, L is n-propylene, R$^5$ is hydrogen and R$^6$ is hydroxyl, or R$^5$ and R$^6$ taken together form =O, and (I) R$^7$ is hydrogen and R$^8$ is a protecting group (see Example 6; the protecting group is t-Boc), or (2) $R^7$ and $R^8$ are both hydrogen and the primary amino group thus present is associated with an organic acid (see Example 7; the organic acid is trifluoroacetic acid), such that the compound is in the form of an acid addition salt.

A compound of the invention may be administered in the form of a salt, ester, amide, prodrug, active metabolite, analog, or the like, provided that the salt, ester, amide, prodrug, active metabolite, or analog is pharmaceutically acceptable and pharmacologically active in the present context. Salts, esters, amides, prodrugs, active metabolites, analogs, and other derivatives of the active agents may be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992).

For example, acid addition salts may be prepared from a free base (e.g., a compound containing a primary amino group) using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of any acidic moieties that may be present may be carried out in a similar manner using a pharmaceutically acceptable base such as sodium hydroxide, potassium hydroxide, ammonium hydroxide, calcium hydroxide, trimethylamine, or the like. Preparation of esters involves reaction of a hydroxyl group with an esterification reagent such as an acid chloride. Amides may be prepared from esters, using suitable amine reactants, or they may be prepared from an anhydride or an acid chloride by reaction with ammonia or a lower alkyl amine. Prodrugs, conjugates, and active metabolites may also be prepared using techniques known to those skilled in the art or described in the pertinent literature. Prodrugs and conjugates are typically prepared by covalent attachment of a moiety that results in a compound that is therapeutically inactive until modified by an individual's metabolic system.

Preferred analogs herein are acid addition salts formed by association of a primary amino group at $-NR^7R^8$ (wherein $R^7$ and $R^8$ are hydrogen) and an acid as set forth above.

In addition, those novel compounds containing chiral centers can be in the form of a single enantiomer or as a racemic mixture of enantiomers. The description is intended to cover both instances.

Representative compounds of the invention may be synthesized using the following general scheme:

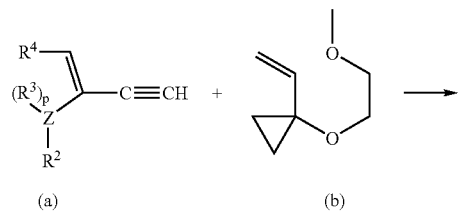

(a)        (b)

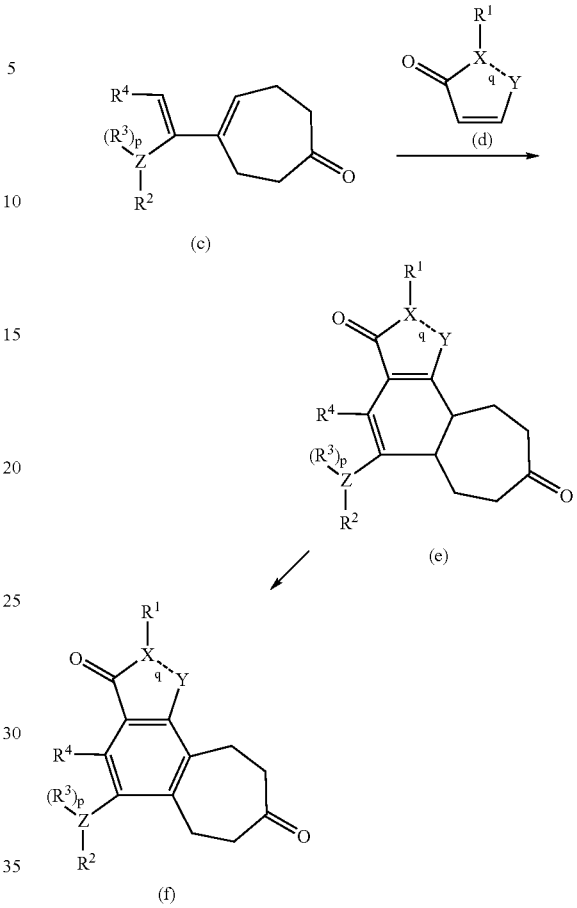

The initial reactant is an ethynyl-substituted olefin (a), which undergoes a [5+2] cycloaddition reaction with the vinylcyclopropane compound (b) to give (c). In this reaction, $R^2$, $R^3$, $R^4$, and p are as defined elsewhere herein, although for an optimal yield, it is preferred that $R^2$ is hydrogen. The reaction is carried out catalytically under an inert atmosphere at a somewhat elevated temperature; optimally, the reaction is conducted using an organometallic catalyst. Such a reaction is described in part (e) of Example 1 using 2-ethynylindole and the vinylcyclopropane shown above, catalyzed by the rhodium complex $[Rh(CO)_2Cl]_2$ (preparation of 2-ethynylindole is described in parts (a) through (d) of Example 1).

Compound (c) (e.g., compound 8 in Example 1) then undergoes a [4+2] cycloaddition (Diels-Alder) reaction with the α,β-unsaturated ketone (d) to result in (e). This reaction is carried out in an inert atmosphere at an elevated temperature, generally at reflux, preferably using molecular sieves or an alternate means of activating the dienophile (d). Part (f) of Example 1 describes such a reaction step, in which the 2-vinylindole 8 and N-methylmaleimide undergo a Diels-Alder reaction followed by double bond isomerization to form the tetrahydrocarbazole 9.

The intermediate compound (e) in the above scheme is then aromatized using known techniques, e.g., by treatment with 2,3-dichloro-5,6-dicyano-1,4-benzoquinone (DDQ); see part (g) of Example 1 describing synthesis of 10. In the product (f), above, any nonhydrogen substituent at $R^1$, e.g., a methyl group, may be removed by treatment with a strong base, followed by hexamethyldilsazane (see Example 2).

The ketone functionality on the cycloheptene ring in compound (f) may be converted to a hydroxyl group using conventional reducing agents, e.g., sodium borohydride, as described in Example 3.

In addition, nonhydrogen substituents on the heteroatom Z are generally introduced after synthesis of compound (f) is complete; see, e.g., Example 4.

Derivatives and analogs of the compounds of the invention may be synthesized using by modifying the methods described herein in ways that will be known to those of ordinary skill in the art and/or are described in the pertinent texts and literature.

III. Utility, Testing, and Administration

The compounds of the present invention are useful as therapeutic agents in the treatment of any condition, disease or disorder that is responsive to the administration of a kinase inhibitor, particularly an inhibitor of PKC. The compounds can be administered to a human patient by themselves or in pharmaceutical compositions in which they are mixed with suitable carriers or excipient(s). Compounds of the invention may also be administered in combination, in which case they may be administered separately, in different dosage forms, or simultaneously, either in one dosage form or in two different dosage forms.

Pharmaceutical formulations suitable for use in conjunction with the present invention include compositions wherein the active agent is contained in a "therapeutically effective" amount, i.e., in an amount effective to achieve its intended purpose. Determination of a therapeutically effective amount for any particular kinase inhibitor of the invention is well within the capability of those skilled in the art. That is, for any of the present kinase inhibitors, a therapeutically effective dose can be estimated initially from cell culture assays. For example, a dose can be formulated to achieve a circulating concentration range that includes an $IC_{50}$ value as determined in cell culture (i.e., the concentration of the test compound required to reduce enzyme activity by 50%). Such information can be used to more accurately determine useful doses in humans.

Toxicity and therapeutic efficacy of the compounds described herein can be determined by standard pharmaceutical procedures in cell cultures or experimental animals, e.g., procedures used for determining the maximum tolerated dose (MTD), the $ED_{50}$, which is the effective dose to achieve 50% of maximal response, and the therapeutic index (TI), which is the ratio of the MTD to the $ED_{50}$. Obviously, compounds with high TIs are the most preferred kinase inhibitors herein, and preferred dosage regimens are those that maintain plasma levels of the active agent at or above a minimum concentration to maintain the desired therapeutic effect. Dosage will, of course, also depend on a number of factors, including the particular kinase inhibitor, the site of intended delivery, the route of administration, and other pertinent factors known to the prescribing physician. Generally, however, dosage will be in the range of approximately 0.1 µg/kg/day to 100 mg/kg/day, more typically in the range of about 1.0 mg/kg/day to 10 mg/kg/day.

The compounds of the invention are useful as kinase inhibitors, or as starting materials or intermediates useful in the synthesis of a kinase inhibitor. In addition to their utility in a method for inhibiting kinases per se, then, the kinase inhibitors of the invention are also useful in methods for treating conditions, diseases, and disorders in which the activity of certain kinases, e.g., PKC, has been found to have a role. These conditions, diseases, and disorders, include cancer, atherosclerosis, diabetes, disorders of the central nervous system (CNS), and autoimmune diseases such as rheumatoid arthritis, and effective treatment according to the invention involves administration to a mammalian individual in need of treatment, generally a human patient, of a therapeutically effective amount of a compound of the invention. The compound is generally administered in a pharmaceutically acceptable formulation as described infra.

In one specific example, the compounds of the invention find use as anticancer agents in mammalian subjects. Representative cancer conditions and cell types against which the compounds of the invention may be useful include melanoma, myeloma, chronic lymphocytic leukemia (CLL), AIDS-related lymphoma, non-Hodgkin's lymphoma, colorectal cancer, renal cancer, prostate cancer, cancers of the head, neck, stomach, esophagus, anus, or cervix, ovarian cancer, breast cancer, peritoneal cancer, and non-small cell lung cancer. A compound of the invention can be administered alone, i.e., in monotherapy, or in combination with one or more other active agents, e.g., other anticancer agents.

The compounds of the invention can also be used to strengthen the immune system of a mammalian subject, wherein a compound of the invention is administered to the subject in an amount effective to increase one or more components of the immune system. For example, strengthening of the immune system can be evidenced by increased levels of T cells, antibody-producing cells, tumor necrosis factors, interleukins, interferons, and the like. Effective dosages may be comparable to those for anticancer uses, and can be optimized with the aid of various immune response assay protocols such as are known in the art (e.g., see Kraft et al. (1996) *Cancer Chemother. Pharmacol.* 37:271–278; Lind et al. (1993) *Surgical Oncol.-Oxford* 2:273–282; and U.S. Pat. No. 5,358,711 to May et al.). The compound can be administered prophylactically, e.g., for subjects who are about to undergo anticancer therapies, as well as therapeutically, e.g., for subjects suffering from microbial infection, bum victims, subjects with diabetes, anemia, radiation treatment, or anticancer chemotherapy. The immunostimulatory activity of the compounds of the present invention is unusual among anticancer compounds and provides a dual benefit for anticancer applications. First, the immunostimulatory activity allows the compounds of the invention to be used in greater doses and for longer periods of time than would be possible for compounds of similar anticancer activity but lacking immunostimulatory activity. Second, the compounds of the present invention can offset the immunosuppressive effects of other drugs or treatment regimens when used in combination therapies.

In practicing various aspects of the present invention, compounds in accordance with the invention can be tested for a biological activity of interest using any assay protocol that is predictive of activity in vivo. For example, a variety of convenient assay protocols are available that are generally predictive of PKC inhibitory activity in vivo. In one approach, PKC inhibitory activity can be assessed using the PKC assay described in Example 9 (also described by Toullec et al. (1991) *J. Biol. Chem.* 266:15771). In that assay, the PKC was derived, as a mixture of isozymes, from rat brains, and activity was determined by incorporation of $^{32}P$ radiolabeled phosphate, derived from $[\gamma\text{-}^{32}P]$-ATP, onto a PKC substrate. Another assay for assessing PKC inhibitory activity is described in Example 10; see also U.S. Patent Application Publication No. 2002/0137789 A1 to Wender et al. In this assay, $K_i$ values are determined for potential inhibitors based on competition with radiolabeled phorbol 12,13-dibutyrate for binding to a mixture of PKC isozymes.

A useful method for assessing anticancer activities of compounds of the invention involves the multiple-human cancer cell line screening assays run by the National Cancer Institute (e.g., Boyd, "Status of the NCI Preclinical Antitumor Drug Discover Screen" in *Cancer: Principles and Practice of Oncology Updates*, DeVita et al., eds, pp. 1–12 (1989)). The screening panel, which involves approximately 60 different human cancer cell lines, is a useful indicator of in vivo antitumor activity for a broad variety of tumor types (Grever et al. (1992) *Seminars Oncol.* 19:622; Monks et al. (1991) *J. Natl. Cancer Inst.* 83:757–766), such as leukemia, non-small cell lung, colon, central nervous system (CNS), melanoma, ovarian, renal, prostate, and breast cancers. Antitumor activity can be expressed in terms of $ED_{50}$ (or $GI_{50}$), where $ED_{50}$ is the molar concentration of compound effective to reduce cell growth by 50%. Compounds with lower $ED_{50}$ values tend to have greater anticancer activities than compounds with higher $ED_{50}$ values. Example 7 of U.S. Patent Application Publication No. 2002/0137789, noted above, describes a P388 murine lymphocytic leukemia cell assay which measures the ability of compounds of the invention to inhibit cellular growth.

Upon the confirmation of a compound's potential activity in the above in vitro assays, further evaluation is typically conducted in vivo in laboratory animals, for example, measuring reduction of lung nodule metastases in mice with B16 melanoma (e.g., Schuchter et al, 1991). The efficacy of drug combination chemotherapy can be evaluated, for example, using the human B-CLL xenograft model in mice (e.g., Mohammad et al, 1996). Ultimately, the safety and efficacy of compounds of the invention are evaluated in human clinical trials.

Experiments conducted in support of the present invention demonstrate that compounds of the present invention exhibit high potencies in several anticancer assays, as summarized in the Examples.

Administration of a compound of the invention may be carried out using any appropriate mode of administration. Thus, administration can be, for example, oral, parenteral, transdermal, transmucosal (including rectal and vaginal), sublingual, by inhalation, or via an implanted reservoir in a dosage form. The term "parenteral" as used herein is intended to include subcutaneous, intravenous, and intramuscular injection.

Depending on the intended mode of administration, the pharmaceutical formulation may be a solid, semi-solid or liquid, such as, for example, a tablet, a capsule, a caplet, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in *Remington: The Science and Practice of Pharmacy* (Easton, Pa.: Mack Publishing Co., 1995). For those compounds that are orally active, oral dosage forms are generally preferred, and include tablets, capsules, caplets, solutions, suspensions and syrups, and may also comprise a plurality of granules, beads, powders, or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms for those kinase inhibitors that are orally active, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy*, cited supra, which describes materials and methods for preparing encapsulated pharmaceuticals.

Oral dosage forms, whether tablets, capsules, caplets, or particulates, may, if desired, be formulated so as to provide for gradual, sustained release of the active agent over an extended time period. Generally, as will be appreciated by those of ordinary skill in the art, sustained release dosage forms are formulated by dispersing the active agent within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations according to this invention for parenteral administration include sterile aqueous and nonaqueous solutions, suspensions, and emulsions. Injectable aqueous solutions contain the active agent in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

The compounds of the invention may also be administered through the skin using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

In addition to the formulations described previously, the compounds may also be formulated as a depot preparation for controlled release of the active agent, preferably sustained release over an extended time period. These sustained release dosage forms are generally administered by implantation (e.g., subcutaneously or intramuscularly or by intramuscular injection).

Although the present compositions will generally be administered orally, parenterally, transdermally, or via an implanted depot, other modes of administration are suitable as well. For example, administration may be rectal or vaginal, preferably using a suppository that contains, in addition to the active agent, excipients such as a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol.

It is to be understood that while the invention has been described in conjunction with the preferred specific embodiments thereof, the description above as well as the examples that follow are intended to illustrate and not limit the scope of the invention. Other aspects, advantages, and modifications within the scope of the invention will be apparent to those skilled in the art to which the invention pertains.

All patents, patent applications, journal articles, and other reference cited herein are incorporated by reference in their entireties.

IV. EXPERIMENTAL

Unless noted otherwise, materials were obtained from commercially available sources and used without further purification. Tetrahydrofuran and diethyl ether were distilled from sodium benzophenone ketyl under a nitrogen atmosphere. Deuterated NMR solvents were dried over $\frac{1}{16}$" bead 4 Å molecular sieves.

All operations involving moisture-sensitive materials were conducted in oven- and/or flame-dried glassware under an atmosphere of anhydrous nitrogen. Hygroscopic solvents and liquid reagents were transferred using dry Gastight™ syringes or cannulating needles. When rigorous exclusion of dissolved oxygen was required, solvents were degassed via consecutive freeze, pump, and thaw cycles, or via an inert gas purge.

Nuclear magnetic resonance (NMR) spectra were recorded on a Varian UNITY INOVA-500, XL400, or Gemini-300 magnetic resonance spectrometer. $^1$H chemical shifts are given in parts per million (δ) downfield from tetramethylsilane (TMS) using the residual solvent signal ($CHC_3$=δ 7.27, benzene=δ 7.15, acetone=δ 2.04) as internal standard. Proton ($^1$H) NMR information is tabulated in the following format: number of protons, multiplicity (s, singlet; d, doublet; t, triplet; q, quartet; sept, septet, m, multiplet), coupling constant(s) (J) in hertz and, in cases where mixtures are present, assignment as the major or minor isomer, if possible. The prefix "app" is occasionally applied in cases where the true signal multiplicity was unresolved and "br" indicates that the signal in question was broadened. Proton decoupled $^{13}$C NMR spectra are reported in ppm (δ) relative to residual $CHCl_3$ (δ 77.25) unless noted otherwise.

Infrared spectra were recorded on a Perkin-Elmer 1600 series FTIR using samples prepared as thin films between salt plates. High-resolution mass spectra (HRMS) were recorded at the NIH regional mass spectrometry facility at the University of California, San Francisco. Fast Atom Bombardment (FAB) high-resolution mass spectra were recorded at the University of California, Riverside. Combustion analyses were performed by Desert Analytics, Tucson, Ariz., 85719 and optical rotations were measured on a Jasco DIP-1000 digital polarimeter.

Flash chromatography was performed using E. Merck silica gel 60 (240–400 mesh) according to the protocol of Still et al. (1978) *J. Org. Chem.* 43:2923. Thin layer chromatography was performed using precoated plates purchased from E. Merck (silica gel 60 PF254, 0.25 mm) that were visualized using either a p-anisaldehyde or Ce(IV) stain.

In these examples and throughout this patent, unless otherwise stated, the abbreviations employed have their generally accepted meanings, as follows:
Boc=t-butoxycarbonyl
$CH_2Cl_2$=methylene chloride
DCE=1,1-dichloroethane
DDQ=2,3-dichloro-5,6-dicyano-1,4-benzoquinone
DME=1,2-dimethoxyethane
DMF=dimethyl formamide
DMSO=dimethyl sulfoxide
$Et_2O$=diethyl ether
EtOAc=ethyl acetate
HCl=hydrochloric acid
HMDS=hexamethyl disilazane
iPrOH=isopropanol
KF=potassium fluoride
KOH=potassium hydroxide
MeCN=acetonitrile
MeOH=methanol
$MgSO_4$=magnesium sulfate
$NaBH_4$=sodium borohydride
NaH=sodium hydride
$NaHCO_3$=sodium carbonate NaOH=sodium hydroxide
Na$_2$SO$_4$=sodium sulfate
PMA=phorbol myristate acetate
Pd(PPh$_3$)$_2$Cl$_2$=bis-triphenylphosphine palladium dichloride
PDBU=phorbol 12, 13-dibutyrate
SEM=2-(trimethylsilyl)ethoxymethyl
TBAF=tetrabutylammonium fluoride
TFA=trifluoroacetic acid
THF=tetrahydrofuran
TLC=thin layer chromatography

EXAMPLE 1

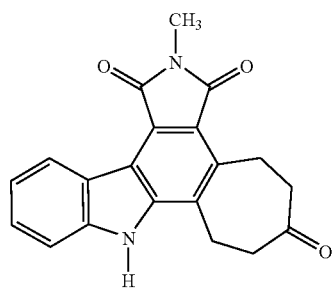

10

Compound 10 was synthesized as follows:
(a) Synthesis of N-protected indole 2 from indole 1:

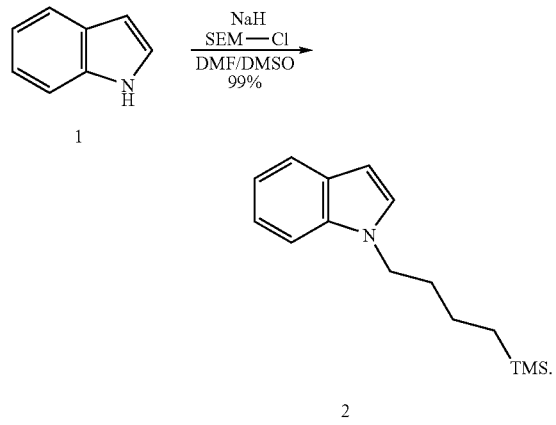

A 1 L flask under a positive pressure of dry nitrogen was charged with NaH (5.81 g, 60%, 145 mmol). The NaH was washed with pentane (1×40 mL) and suspended in DMF (240 mL) and DMSO (48 mL). The reaction was chilled to 0° C. Indole, 1, (10.16 g, 86.7 mmol) was added portionwise over 15 min. The reaction was purged with nitrogen for 15 min and then left attached to only a bubbler. The reaction was allowed to warm to rt and stirred for 2.5 h at which point gas evolution was no longer observed. The reaction was chilled again to 0° C. and SEM-Cl (16 mL, 90.4 mmol) was added portionwise over 15 min. The reaction was stirred at 0° C. for 5 min, then allowed to warm to room temperature and stirred for 2 h, at which point the reaction was complete as determined by TLC. The reaction was poured into ice water (400 mL) and extracted with Et$_2$O (3×400 mL). The combined organics were washed with water (200 mL) and brine (200 mL), Dried (Na$_2$SO$_4$), filtered and reduced to a slightly yellow oil. The residue was purified by flash column chromatography (petroleum ether/Et$_2$O 9:1, eluant) affording 21.12 g of 2 (99%) as a colorless oil that solidified in the freezer.

Data for 2: $^1$H NMR (300 MHz, CDCl$_3$, δ): −0.05 (s, 9H), 0.89 (t, J=8.3 Hz, 2H), 3.47 (t, J=8.3 Hz, 2H), 5.49 (s, 2H), 6.53 (dd, J=3.1, 0.7 Hz, 1H), 7.13–7.18 (m, 2H), 7.21–7.6 (m, 1H), 7.50 (d, J=8.3 Hz,1H) 7.63 (d, J=7.8 Hz, 1H). $^{13}$C NMR (75 MHz, CDCl$_3$, δ): −1.46, 17.67, 65.71, 75.55, 102.37, 109.91, 120.08, 120.87, 122.00, 127.99, 129.02, 136.31. IR (KBr): 2952.7, 2893.2, 1516.3, 1462.2, 1303.0, 1248.7, 1076.6, 859.5, 835.8, 739.3 cm$^{-1}$. HRMS (m/z): [M$^+$] calcd for C$_{14}$H$_{21}$NOSi, 247.1392; found, 247.1396. Elemental Analysis: Calcd for C$_{14}$H$_{21}$NOSi: C, 67.96; H, 8.56; N, 5.66. Found: C, 68.00; H, 8.50; N, 5.43.

(b) Synthesis of stannane 3 from N-protected indole 2:

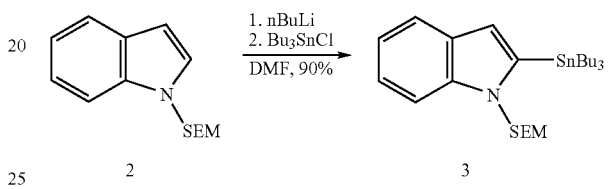

N-protected indole 2 (21.01 g, 84.9 mmol) was dissolved in DME (200 mL) under a positive pressure of dry nitrogen. The reaction was chilled to −10° C. n-BuLi (66 mL, 1.40 M in hexanes, 92.4 mmol) was added dropwise over 20 min while maintaining the reaction temperature at −10° C. The reaction temperature was maintained at −10° C. for 15 min and then cooled to −20° C. Tri(n-butyl)tin chloride (25 mL, 96%, 88.5 mmol) was added dropwise over 10 min while maintaining the reaction temperature at −20° C. The reaction was allowed to warm to 0° C. at which point the dry ice acetone bath was exchanged for an ice bath. The reaction was stirred for 2.5 h at 0° C. The reaction was poured in ice water (500 mL) and extracted with Et$_2$O (3×500 mL). The combined organics were washed with water (400 mL) and brine (400 mL), Dried (Na$_2$SO$_4$), filtered and reduced to a bright yellow oil. Distillation (0.02 mmHg, 180° C.) afforded 41.08 g of 3 (90%) as a bright yellow oil.

Data for 3: $^1$H NMR (500 MHz, CDCl$_3$, δ): −0.05 (s, 9H), 0.88–0.093 (m, 11H), 1.13–1.64 (m, 6H), 1.31–1.39 (m, 6H), 1.52–1.58 (m, 6H), 3.41–3.45, (m, 2H), 5.46 (s, 2H), 6.63–6.66 (m, 2H), 7.09 (t, J=7.5 Hz,1H), 7.16–7.19 (m, 1H), 7.45 (d, J=8.3 Hz,1H), 7.58 (d, J=7.5 Hz, 1H). $^{13}$C NMR (125 MHz, CDCl$_3$, δ): −1.45, 10.42, 13.68, 17.89, 27.36, 29.05, 65.45, 76.18, 109.28, 113.73, 119.50, 119.88, 121.41, 129.56, 139.81, 141.88. IR (film): 2955.4, 2923.7, 2871.8, 2854.2, 1519.1, 1464.0, 1435.4, 1375.7, 1340.5, 1310.0, 1297.9, 1249.3, 1166.5, 1076.6, 1027.8, 920.1, 859.8, 835.6, 788.2, 747.6, 734.5, 693.1, 665.5 cm$^{-1}$. HRMS (m/z): [M$^+$-Bu] calcd for C$_{22}$H$_{38}$NOSiSn, 480.1745; found, 480.1752. bp: 180° C., 0.02 mm Hg.

(c) Synthesis of N-protected 2-ethynyl indole 5:

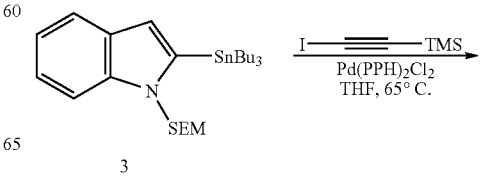

3

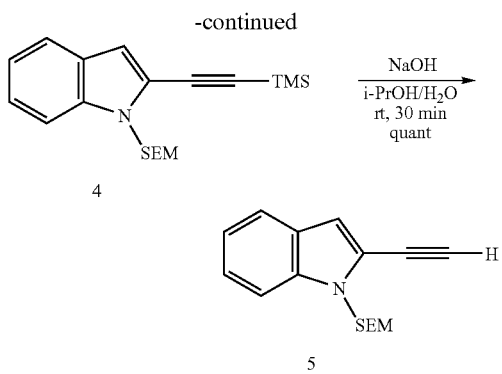

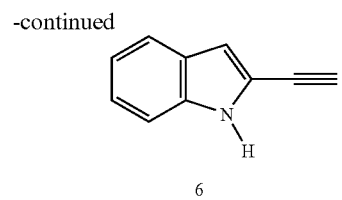

A 2-neck, 500 mL flask equipped with a reflux condenser and dropping funnel was charged with Pd(PPh$_3$)$_2$Cl$_2$ (748.1 mg, 98%, 1.0 mmol) under a positive pressure of dry nitrogen. Dry THF (200 mL was added by cannula, followed by 1-iodo-2-(trimethylsilyl)acetylene (10.98 g, 48.99 mmol). The reaction was heated to reflux by a preheated oil bath and stannane 3 in 55 mL of dry THF was added dropwise over 2.5 h. The reaction was monitored by TLC, and was complete 1 h after the addition of stannane was complete. The reaction was cooled to room temperature, diluted with EtOAc (750 mL), stirred over 15% KF (aq) (750 mL) for 15 min and filtered through paper. The organic layer was isolated and the aqueous layer extracted with Et$_2$O (3×300 mL). The combined organics were washed with water (500 mL) and brine (500 mL), dried (Na$_2$SO$_4$), filtered and reduced to a dark oil to give crude 4. The crude material was dissolved in iPrOH (75 mL) and 1 M NaOH (aq) (75 mL) and stirred at rt. The reaction was complete within 30 min. The reaction was poured into water (400 mL) and extracted with Et$_2$O (3×400 mL). The combined organics were washed with water (400 mL) and brine (400 mL), Dried (Na$_2$SO$_4$), filtered and reduced to oil. The residue was purified by flash column chromatography (petroleum ether/Et$_2$O 9:1 eluant) afforded 9.00 g of 5 (88%, two steps) as a colorless oil. Analytical TLC indicated a single compound (10% Et$_2$O in petroleum ether eluant, R$_f$=0.48).

Data for 5: $^1$H NMR (500 MHz, CDCl$_3$, δ): −0.06 (s, 9H), 0.88–0.91 (m, 2H), 3.50 (s, 1H), 3.53–3.56 (m, 2H), 5.64 (s, 2H), 6.86 (s, 1H), 7.15–7.18 (m,1H), 7.28–7.31 (m, 1H), 7.48 (dd, J=8.3, 0.5 Hz, 1H), 7.57–7.60 (m, 1H). $^{13}$C NMR (75 MHz, CDCl$_3$, δ): -1.49, 17.69, 65.74, 73.02, 75.33, 83.75, 109.93, 110.43, 120.62, 120.98, 121.07, 123.82, 127.29, 136.86. IR (film): 3305.0, 2952.5, 2894.6, 2107.9, 1452.7, 1390.0, 1334.9, 1312.6, 1248.7, 1162.4, 1115.0, 1091.6, 1076.7, 930.2, 900.2, 859.4, 835.7, 794.0, 747.7, 692.5 cm$^{-1}$. HRMS (m/z): [M+] calcd for C$_{16}$H$_{21}$NOSi, 271.1392; found, 271.1385.

(d) Deprotection of 5 to give 2-ethynyl indole 6:

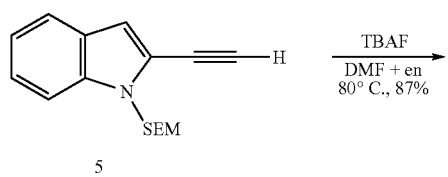

TBAF (100 mL, 1.0 M in THF, 100 mmol) was added to a 250 mL flask and reduced to a solid by rotary evaporation at room temperature. 5 (8.76 g, 32.3 mmol) in DMF (100 mL) was added to the flask. Ethylene diamine (10 mL, 148 mmol) was added by syringe. The reaction was purged with nitrogen and heated to 80° C. overnight. The reaction was diluted with EtOAc (500 mL) and washed with 0.1 M HCl (aq). The aqueous layer was extracted with EtOAc (250 mL) and Et$_2$O (250 mL). The combined organics were washed with water (500 mL) and brine (500 mL), dried (MgSO$_4$), filtered and reduced to oil. The residue was purified by flash column chromatography (petroleum ether/Et$_2$O 7:3 eluant) afforded 3.95 g of 6 (87%) as a white crystalline solid. 6 could be further purified by crystallization from hexane or sublimated (mp=64–65° C.).

Data for 6: $^1$H NMR (300 MHz, CDCl$_3$, δ): 3.32 (s, 1H), 6.82 (d, J=1.2 Hz, 1H), 7.10–7.15 (m, 1H), 7.22–7.27 (m, 1H+CHCl$_3$), 7.32 (dd, J=8.3, 1.0 Hz, 1H), 7.57–7.61 (m, 1H), 8.18 (br s, 1H, NH). $^{13}$C NMR (75 MHz, CDCl$_3$, δ): 76.19, 80.83, 109.65, 110.81, 117.46, 120.57, 120.98, 123.79, 127.27, 135.83. IR (film): 3389.5, 3283.2, 2112.2, 1449.9, 1400.1, 1348.1, 1294.9, 1236.3, 1129.8, 1016.6, 797.6, 753.6, 742.0, 681.9, 654.9 cm$^{-1}$. HRMS (m/z): [M+] calcd for C$_{10}$H$_7$N, 141.0578; found, 141.0574. Elemental Analysis: Calcd for C$_{10}$H$_7$N: C, 85.08; H, 5.00; N, 9.92. Found: C, 84.97; H, 5.25; N, 9.77. mp: 64–65° C. (opened and sealed mp tube).

(e) Synthesis of 8:

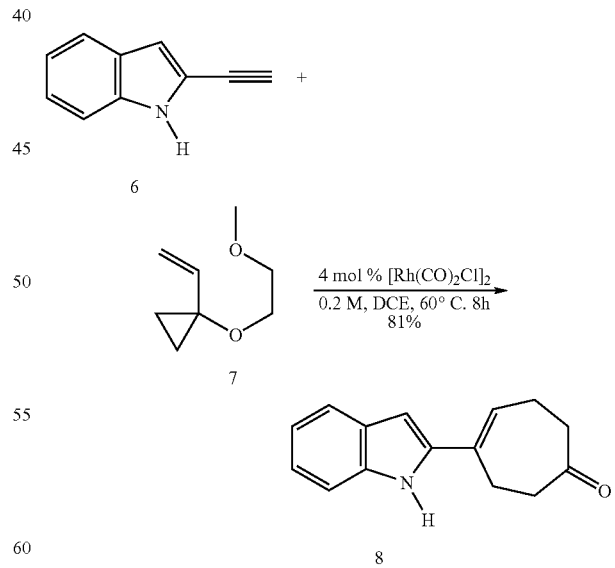

An oven dried, septum capped 16×100 mm, borosilicate glass test tube, under a positive pressure of dry argon, was charged with [Rh(CO)$_2$Cl]$_2$ (4.0 mg, 0.01 mmol) and 2-ethynylindole 6 (36.5 mg, 0.25 mmol). DCE (1.25 mL) and vinylcyclopropane 7 (58.7 mg, 0.41 mmol) were added by syringe. The reaction was purged with argon for 15 min and then maintained under a positive argon pressure. The reaction was stirred at room temperature and monitored by TLC. The reaction was complete after 8 h and hydrolyzed with 1% HCl in MeOH (0.5 mL). The resultant mixture was filtered through a short pad of silica gel (Et$_2$O eluant) and concentrated in vacuo. The residue was purified by flash column chromatography (gradient Et$_2$O 50% 100% in petroleum ether) affording 46.0 mg (81%) of 8 as an amorphous solid. Analytical TLC indicated a single compound (Et$_2$O eluant, $R_f$=0.54).

Data for 8: $^1$H NMR (300 MHz, CDCl$_3$, δ): 2.56–2.62 (m, 2H), 2.65–2.71 (m, 2H), 2.75–2.78 (m, 2H), 2.84–2.86 (m, 2H), 6.27 (t, J=5.9 Hz, 1H), 6.51 (d, J=1.7 Hz, 1H), 7.08 (t, J=7.3 Hz, 1H), 7.18(t,J=7.6 Hz, 1H), 7.32(d, J=8.1 Hz, 1H), 7.56 (d, J=7.8 Hz, 1H), 8.11 (brs, 1H, N-Hk). $^3$C NMR (75 MHz, CDCl$_3$, δ): 23.80, 25.78, 40.60, 42.22, 100.19, 110.49, 119.96, 120.51, 122.51, 124, 10, 128.64, 133.53, 136.52, 128.84, 212.57. IR (film): 3369.7, 3055.0, 2949.2, 1698.0, 1454.8, 1416.0, 1344.8, 1296.2, 1232.5, 1203.4, 1164.1, 1011.5, 784.9, 748.5 cm$^{-1}$. HRMS (m/z): [M+] calcd for C$_{15}$H$_{15}$NO, 225.1154; found, 225.1155.

(f) Synthesis of 9:

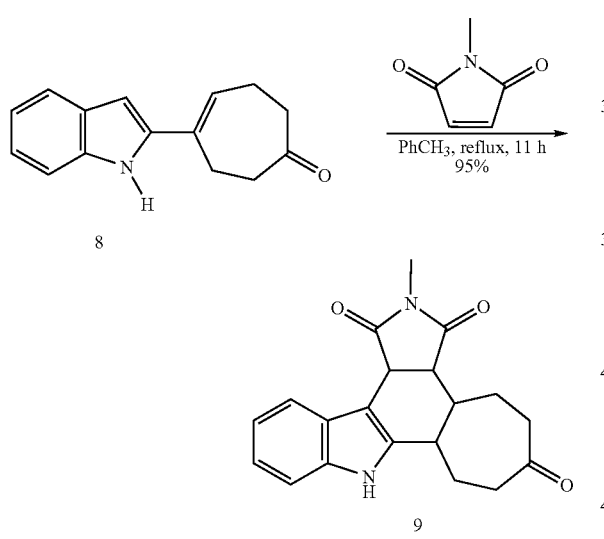

A 25 mL reaction flask, under a positive pressure of dry argon, was charged with vinylindole 8 (137.9 mg, 0.61 mmol), N-methylmaleimide (126.9 mg, 1.1 mmol) and powered 4A MS (1.81 g). Toluene (6.1 mL) was added. The reaction was heated to reflux and monitored by TLC. The reaction was complete after 11 h. The molecular sieves were filtered off and washed with EtOAc (50 mL). The filtrate was concentrated in vacuo. The residue was purified by flash column chromatography (80% EtOAc in petroleum ether eluant) afforded 194.7 mg of 9 (95%) as an amorphous solid. Analytical TLC indicated a single compound (EtOAc eluant, $R_f$=0.61).

Data for 9: $^1$H NMR (500 MHz, CDCl$_3$, δ): 1.70–1.78 (m, 1H), 1.95–1.98 (m, 1H), 2.19–2.22 (m, 1H), 2.47–2.57 (m, 2H), 2.67–2.76 (m, 2H), 2.84–3.06 (m, 6H), 3.40 (dd, J=7.6, 3.9 Hz, 1H), 4.38 (dd, J=7.6, 1.8 1H), 7.17–7.21 (m, 2H), 7.30–7.32 (m, 1H), 7.97–8.00 (m, 2H). $^{13}$C NMR (75 MHz, CDCl$_3$, δ): 24.55, 27.51, 28.24, 38.41, 41.33, 41.39, 43.15, 43.56, 47.52, 104.51, 110.75, 120.10, 120.47, 122.50, 126.44, 135.86, 136.44, 176.49, 177.65, 213.00. IR (film): 3370.2, 3057.7, 2945.9, 2251.4, 1771.3, 1696.7, 1584.3, 1492.0, 1458.8, 1433.7, 1383.2, 1346.5, 1318.4, 1289.7, 1238.3, 1158.0, 1118.5, 1100.9, 1027.5, 1009.9, 957.2, 909.7, 844.0, 811.1, 792.5, 731.2, 648.2 cm$^{-1}$.

HRMS (m/z): [M+] calcd for C$_{20}$H$_{20}$N$_2$O$_3$, 336.1474; found, 336.1474.

(g) Synthesis of 10:

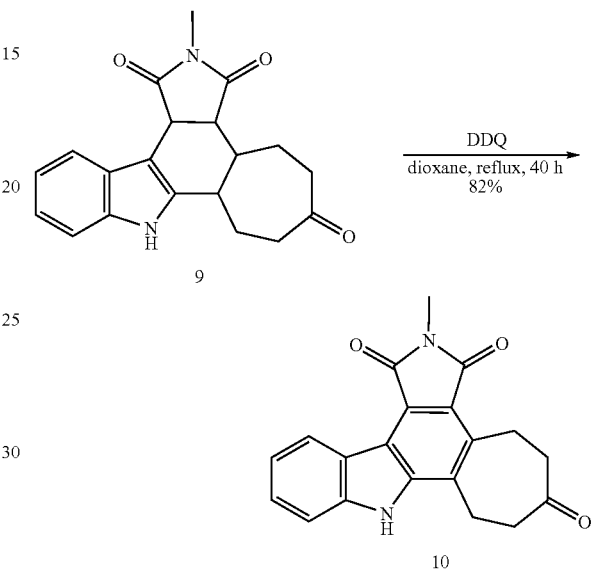

A 500 mL flask was charged with tetrahydrocarbazole 10 (661.2 mg, 1.97 mmol) and DDQ (1.37 g, 5.9 mmol) under a positive pressure of dry argon. Dioxane (200 mL) was added to give a dark green solution. The reaction was heated to reflux for 40 h. The reaction mixture was reduced to 1/10 of the initial volume and diluted with EtOAc (500 mL). The organic layer was washed with sat NaHCO$_3$ (2×250 mL), water (250 mL) and brine (250 mL). The aqueous layers were back extracted with EtOAc (250 mL). The combined organic layers were dried (MgSO$_4$) and filtered. The dried solution was reduced to dryness and the bright yellow powder was washed with CH$_2$Cl$_2$ (3×50 mL) affording 538.8 mg of 10 (82%). Analytical TLC indicated a single compound (80% EtOAc in petroleum ether eluant, $R_f$=0.56).

Data for 10: $^1$H NMR (500 MHz, DMSO-d$_6$, δ): 2.59–2.61 (m, 2H), 2.66–2.68 (m, 2H), 3.07 (s, 3H) 3.32–3.34 (m, 2H+H$_2$O), 3.67–3.70 (m, 2H), 7.29 (dt, J=1.2, 7.4 Hz,1H), 7.53–7.59 (m, 2H), 8.83 (d, J=8.1 Hz, 1H), 11.92 (s, 1H, N-H). $^{13}$C NMR (75 MHz, DMSO-d$_6$, δ): 21.41, 22.36, 23.51, 43.50, 43.02, 111.62, 116.89, 120.05, 120.24, 120.81, 124.77, 125.03 128.17, 129.25, 136.84, 141.87, 142.52, 210.82, 219.82, 220.18. IR (KBr): 3350.1, 2917.9, 2849.6, 1750.1, 1690.0, 1630.4, 1612.4, 1499.1, 1459.9, 1436.5, 1374.2, 1331.6, 1260.7, 1232.2, 1168.3, 1049.7, 989.8, 826.0, 754.5, 638.3 cm$^{-1}$. HRMS (m/z): [M$^+$] calcd for C$_{20}$H$_{16}$N$_2$O$_3$, 332.1161; found, 332.1169. mp=309–310° C. (dec.).

EXAMPLE 2

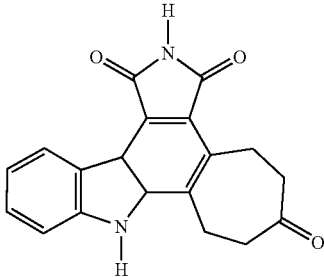

11

Compound 11 was synthesized from 10 as follows:

A 25 mL round bottom flask was charged with N-methylmaleimide carbazole 10 (98.2 mg, 0.30 mmol). Ethanol (10 mL) was added to give a bright yellow suspension. KOH (223.3 mg, 85%, 3.4 mmol) was added. The reaction was purged with nitrogen for 15 min and then maintained under a positive nitrogen pressure. The reaction was allowed to react at room temperature, and slowly became a bright red solution. After 4 h the reaction was complete by TLC. The reaction was diluted with $CH_2Cl_2$ (50 mL) and water (50 mL). The reaction was acidified by the addition of 20% citric acid (20 mL) and stirred for 15 min. The organic layer was isolated and the aqueous layer extracted with $CH_2Cl_2$ (4×50 mL). The combined organics were washed with water (50 mL). The organic layer was reduced to 25 mL and diluted with absolute EtOH (50 mL). The organic layer was reduced and diluted with absolute EtOH (3×50 mL), and finally reduced to dryness to give 91.2 mg (97%) of anhydride as a yellow powder that was taken on without any additional purification. The anhydride was dissolved in 4.5 mL of DMF under a positive pressure of dry nitrogen. In a separate flask HMDS (1.0 mL, 4.7 mmol) and MeOH (100 μL, 2.5 mmol) were combined. The HMDS/MeOH solution was added to the reaction flask. The reaction was purged with nitrogen for 15 min and then maintained under a positive nitrogen pressure. After 18 h at rt, the reaction was heated to 80° C. for 1 h. The reaction was poured into water (10 mL) and extracted with EtOAc (5×10 mL), Dried ($MgSO_4$) and filtered. The solution was reduced to a red solid that was washed with pentane (3×20 mL) and ether (3×20 mL) and dried to give 90.6 mg (97%, two steps) of 11. Analytical TLC indicated a single compound (EtOAc eluant, $R_f$=0.55).

Data for 11: $^1H$ NMR (500 MHz, DMSO-$d_6$, δ): 2.60–2.62 (m, 2H), 2.67–2.69 (m, 2H), 3.36–3.38 (m, 2H), 3.70–3.72 (m, 2H), 7.30 (t, J=7.4 Hz, 1H), 7.55 (t, J=7.6 Hz, 1H), 7.60 (d, J=8.1 Hz, 1H), 8.85 (d, J=7.8 Hz, 1H), 11.11 (s, 1H), 11.96 (s, 1H). $^{13}C$ NMR (75 MHz, DMSO-$d_6$, δ): 21.20, 22.38, 42.51, 43.03, 111.46, 117.20, 120.05, 120.27, 120.61, 124.79, 124.97, 127.91, 129.38, 136.79, 141.58, 142.42, 169.80, 171.42, 209.95. IR (KBr): 3304.2, 3058.3, 2961.2, 1751.8, 1736.0, 1701.9, 1459.9, 1429.8, 1320.2, 1258.3, 1228.2, 1104.0, 1043.5, 758.1, 638.2 $cm^{-1}$. HRMS (m/z): [M+] calcd for $C_{19}H_{14}N_2O_3$, 318.1004; found, 318.1012.

EXAMPLE 3

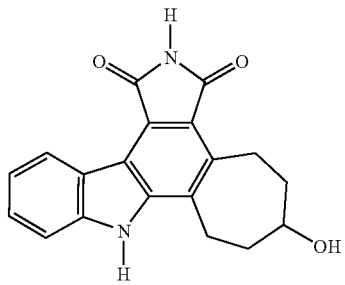

12

Compound 12 was synthesized from 11 as follows:

A 25 mL round bottom flask, under a positive pressure of dry nitrogen, was charged with ketone 11 (15.5 mg, 0.05 mmol). MeOH (5 mL) and $CH_2Cl_2$ (5 mL) were added, dissolving 11. The reaction was chilled to 0° C., and $NaBH_4$ (9.8 mg, 0.26 mmol) was added. After 1 h the reaction was complete by TLC. The reaction was diluted with EtOAc (20 mL) and water (20 mL). The organic layer was isolated and washed with water (2×20 mL). The organic layer was dried ($Na_2SO_4$), filtered, and reduced in vacuo. The residue was purified by flash column chromatography (20% acetone in EtOAc eluant) affording 14.1 mg (90%) of 12 as a bright yellow solid. Analytical TLC indicated a single compound (20% acetone in EtOAc eluant, $R_f$=0.41).

Data for 12: $^1H$ NMR (500 MHz, DMSO-$d_6$, δ): 1.37–1.50 (m, 2H), 1.91–1.96 (m, 2H), 2.89 (dd, J=14.2, 10.7 Hz, 1H) 3.02–3.14 (m, 1H), 3.36–3.41 (m, 1H+$H_2O$), 3.84–3.96 (m, 2H), 4.76 (d, J=7.4 Hz, 1H), 7.25 (t, J=7.4 Hz, 1H), 7.49–7.56 (m, 2H), 8.82 (d, J=8.1 Hz, 1H), 10.94 (br s, 1H), 11.78 (s, 1H). $^{13}C$ NMR (125 MHz, DMSO-$d_6$, δ): 20.85, 22.22, 29.61, 35.06, 55.84, 111.39, 117.00, 119.84, 120.22, 120.74, 124.37, 124.75, 127.78, 131.73, 139.21, 141.63, 142.36, 169.88, 171.66. IR(KBr): 3393.2, 3213.9, 3057.6, 2920.7, 1744.4, 1707.2, 1612.2, 1492.2, 1460.6, 1426.1, 1375.5, 1319.4, 1259.0, 1228.2, 1121.2, 1104.0, 1040.1, 1021.0, 934.0, 903.8, 847.4, 804.2, 760.9, 740.1, 657.8, 638.2 $cm^{-1}$. HRMS (m/z): [M+] calcd for $C_{19}H_{16}N_2O_3$, 320.1161; found, 320.1161.

EXAMPLE 4

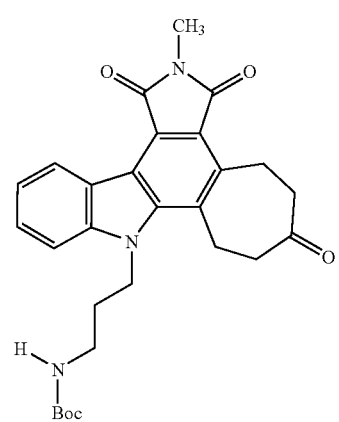

13

Compound 13 was synthesized from 10 as follows:

A 25 mL flask, under a positive pressure of dry nitrogen, was charged with carbazole 10 (96.2 mg, 0.29 mmol), N-(Boc)-protected 1-amino-2-bromoethane (198.8 mg, 0.84 mmol) and $Cs_2CO_3$ (594.4 mg, 1.83 mmol). DMF (6 mL) was added to give a dark red solution and suspended solids. The reaction was purged with nitrogen for 15 min and then maintained under a positive nitrogen pressure. The reaction was heated to 80° C. and monitored by TLC. The reaction was complete within 4 h. The solids of the reaction mixture were filtered off. The filtrate was diluted with water (20 mL) and extracted with EtOAc (5×15 mL). The combined organics were washed with water (15 mL) and brine (15 mL), dried ($MgSO_4$), and filtered. Silica gel chromatography (EtOAc/$CH_2Cl_2$ 1:1 eluant) afforded 121.4 mg of 13 (86%) as a bright yellow solid. Analytical TLC indicated a single compound (EtOAc eluant, $R_f$=0.60).

Data for 13: $^1$H NMR (300 MHz, $CDCl_3$, δ): 1.47 (s, 9H), 2.10–2.20 (m, 2H), 2.72–2.82 (m, 4H), 3.23–3.30 (m, 5H), 3.48–3.52 (m, 2H), 3.83–3.87 (m, 2H), 4.48 (t, J=7.9, 2H), 4.70 (br s, 1H, N-H), 7.35–7.44 (m, 2H), 7.57–7.62 (m, 1H), 9.19 (d, J=7.8 Hz, 1H). $^{13}$C NMR (75 MHz, $CDCl_3$, δ): 21.97, 22.79, 23.71, 28.30, 30.86, 38.11, 38.48, 43.65, 43.83, 44.03, 108.85, 114.29, 120.76, 120.89, 121.30, 125.53, 126.25, 127.31, 128.63, 128.67, 137.82, 138.68, 143.64, 156.14, 156.36, 209.29. IR (film): 3369.6, 2976.0, 1752.7, 1694.1, 1627.5, 1602.1, 1513.8, 1473.3, 1435.5, 1409.4, 1367.3, 1335.7, 1250.2, 1209.5, 1171.7, 1027.3, 996.0, 917.9, 860.1, 753.6, 735.6 $cm^{-1}$.

HRMS (m/z): [M+] calcd for $C_{28}H_{31}N_3O_5$, 489.2264; found, 489.2254.

EXAMPLE 5

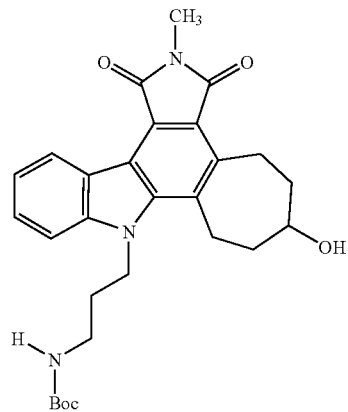

14

Compound 14 was synthesized as follows:

An oven dried, septum capped 16×150 mm disposable, borosilicate glass test tube, under a positive pressure of dry argon, was charged with ketone 13 (111.3 mg, 0.23 mmol) and $CH_2Cl_2$ (11 mL) to give a bright yellow solution. The reaction was cooled to 0° C. $NaBH_4$ (50.5 mg, 1.33 mmol) was added followed by EtOH (11 mL). The reaction was purged with argon for 15 min and then maintained under a positive argon pressure. The reaction was monitored by TLC and was complete within 1.5 h. The reaction was transferred to another flask and re-chilled to 0° C. The reaction was quenched with sat. $NH_4Cl$ (40 mL) and diluted with EtOAc (40 mL). The organic layer was isolated and the aqueous phase extracted with EtOAc (3×40 mL). The combined organics were washed with 0.01 M HCl (40 mL), water (2×40 mL) and brine (40 mL), dried ($MgSO_4$), and filtered. The organic layer was reduced in vacuo. The residue was purified by flash column chromatography (20% acetone in EtOAc) to afford 93.7 mg (84%) of 14 (84%) as a bright yellow powder. Analytical TLC indicated a single compound (EtOAc eluant, $R_f$=0.51).

Data for 14: $^1$H NMR (500 MHz, DMSO-$d_6$, δ): 1.32–1.58 (m, 11H), 1.89–2.04 (m, 3H), 2.06–2.20 (m, 1H), 2.95–3.13 (m, 6H), 3.16–3.26 (m, 1H), 3.51 (dd, J=15.1, 9.5 Hz, 1H), 3.90–3.94 (m, 2H), 4.47 (t, J=7.9 Hz, 2H), 4.78 (d, J=4.4 Hz, 1H), 7.10 (t, J=5.5 Hz,1H), 7.32 (t, J=7.6 Hz, 1H), 7.58 (t, J=7.7 Hz, 1H), 7.70 (d, J=8.5 Hz, 1H), 9.02 (d, J=7.8 Hz, 1H). $^{13}$C NMR (75 MHz, DMSO-$d_6$, δ): 20.96, 21.85, 23.51, 28.24, 30.07, 35.50, 37.17, 37.41, 43.79, 58.50, 77.74, 109.77, 118.86, 119.87, 120.35, 121.31, 123.20, 124.79, 128.14, 131.94, 140.97, 141.45, 143.41, 155.73, 168.28, 169.75. IR (KBr): 3448.2, 3394.7, 2972.0, 2935.1, 1746.3, 1686.5, 1524.5, 1438.1, 1406.6, 1367.9, 1331.8, 1251.7, 1173.0, 1055.7, 997.6, 857.8, 800.1, 752.2, 741.2, 688.0 $cm^{-1}$.

HRMS (m/z): [M$^+$] calcd for $C_{28}H_{33}N_3O_5$, 491.2420; found, 491.2421.

EXAMPLE 6

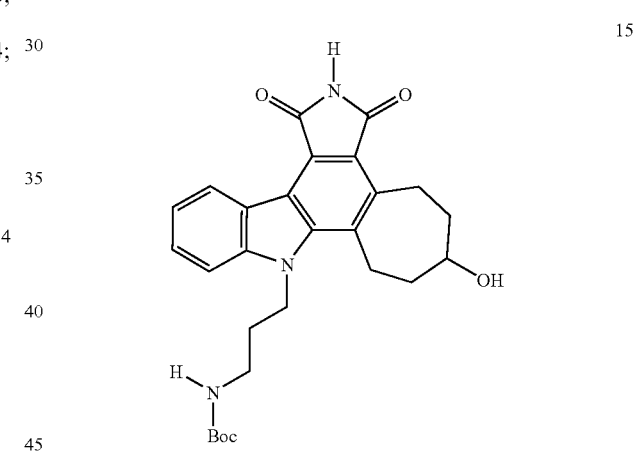

15

Compound 15 was synthesized from 14 as follows:

An oven dried, septum capped 16×150 mm disposable, borosilicate glass test tube, under a positive pressure of dry nitrogen, was charged with alcohol 14 (83.7 mg, 0.17 mmol). Ethanol (3.4 mL) was added to give a bright yellow suspension. KOH (135.0 mg, 85%, 2.0 mmol) was added. The reaction was purged with nitrogen for 15 min and then maintained under a positive nitrogen pressure. The reaction was heated to 80° C., and became a bright red solution within 15 min. After 3 h the reaction was complete by TLC. The reaction was diluted with $CH_2Cl_2$ (35 mL) and water (35 mL). The reaction was acidified by the addition of 20% citric acid (5 mL) and stirred for 15 min. The organic layer was isolated and the aqueous layer extracted with $CH_2Cl_2$ (2×35 mL). The combined organics were washed with water (2×35 mL). The organic layer was reduced to 10 mL and diluted with absolute EtOH (35 mL). The organic layer was reduced and diluted with absolute EtOH (35 mL), and finally reduced to dryness to give a bright yellow powder that was taken on without any additional purification. The crude anhydride was dissolved in 3.5 mL of DMF under a positive pressure of dry nitrogen. In a separate flask HMDS (1.0 mL, 4.7 mmol) and MeOH (100 μL, 2.5 mmol) were combined. The HMDS/MeOH solution was added to the reaction flask. The reaction was purged with nitrogen for 15 min and then maintained under a positive nitrogen pressure. After 18 h at rt, the reaction was poured into water (25 mL) and extracted with EtOAc (5×25 mL). The combined organics were washed with water (2×25 mL) and brine (25 mL), dried (MgSO$_4$) and filtered. The solution was reduced and the residue purified by flask column chromatography (EtOAc eluant) affording 0.7 mg (87%, two steps) of 15 as a bright yellow powder. Analytical TLC indicated a single compound (EtOAc eluant, R$_f$=0.34).

Data for 15: $^1$H NMR (500 MHz, DMSO-d$_6$, δ): 1.32–1.58 (m, 11H), 1.87–2.10 (m, 4H), 2.86–3.15 (m, 4H), 3.43–3.54 (m, 1H), 3.89–3.92 (m, 2H), 4.42–4.48 (m, 2H), 4.76 (d, J=4.2 Hz, 1H), 7.06–7.10 (m, 1H), 7.30 (t, J=7.7 Hz, 1H), 7.57 (t, J=7.7 Hz, 1H), 7.60 (d, J=8.5 Hz, 1H), 9.00 (d, J=7.8 Hz, 1H), 11.06 (s, 1H). $^{13}$C NMR (75 MHz, DMSO-d$_6$, δ): 20.96, 21.86, 23.50, 28.24, 30.07, 35.05, 35.50, 37.41, 43.80, 77.74, 109.74, 119.95, 120.32, 120.56, 123.89, 124.77, 128.12, 131.91, 132.30, 141.07, 141.56, 143.39, 155.71, 168.25, 169.72. IR (film): 3369.5, 2927.7, 1748.4, 1694.3, 1439.2, 1366.7, 1332.0, 1251.1, 1169.8, 1040.2, 758.5 cm$^{-1}$. HRMS (m/z): [M$^+$] calcd for C$_{27}$H$_{31}$N$_3$O$_5$, 477.2264; found, 477.2263.

EXAMPLE 7

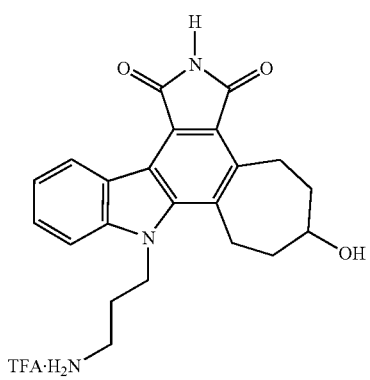

16

Compound 16 was synthesized from 15 as follows:

A 25 mL flask was charged with 15 (75.0 mg, 0.14 mmol) under a positive pressure of dry nitrogen. CH$_2$Cl$_2$ (2 mL) was added to give a yellow suspension. Triisopropylsilane (100 μL, 0.49 mmol) was added followed by TFA (2 mL). The suspension became a dark red solution that was allowed to stir at rt under positive nitrogen pressure overnight. The solvent was removed to give a bright yellow solid that was washed with Et$_2$O (2×5 mL), CH$_2$Cl$_2$ (2×5 mL), and petroleum ether (2×5 mL). The residue was purified by HPLC (5% MeCN→95% MeCN in water+1% TFA) to give 62.2 mg (90%) of 16. Analytical HPLC indicated a single compound (5% MeCN 95% MeCN in water+1% TFA).

Data for 16: $^1$H NMR (500 MHz, DMSO-d$_6$, δ): 1.44–1.64 (m, 2H), 1.82–2.03 (m, 2H), 2.07–2.18 (m, 2H), 2.26–2.32 (m, 1H), 2.95–3.02 (m, 2H), 3.22–3.27 (m, 1H), 3.49–3.57 (m, 2H), 3.86–3.94 (m, 1H), 4.63 (t, J=7.6 Hz, 2H), 4.86 (br s, 1H), 7.34–7.37 (m, 1H), 7.60–7.65 (m, 1H), 7.78-7.81 (m, 1H), 7.89 (br s, 3H, —NH$_3$), 9.05 (d, J=7.8 Hz, 1H), 11.18 (s, 1H). $^{13}$C NMR (75 MHz, DMSO-d$_6$, δ): 23.34, 25.97, 27.69, 30.70, 35.13, 36.26, 42.82, 64.79, 109.80, 116.27 (q, 290.5 Hz, CF$_3$) 119.82, 120.35, 120.66, 124.72, 128.02, 131.91, 132.30, 141.07, 143.43, 144.64, 155.71, 159.20 (q, 37.0 Hz, COCF$_3$) 168.25, 169.72. IR (KBr): 3423.8, 3186.4, 3058.0, 2945.8, 1782.0, 1701.9, 1406.2, 1364.1, 1328.0, 1203.9, 1168.6, 1073.2, 1024.8, 987.8, 971.8, 901.4, 838.0, 800.3, 741.7, 723.1, 670.1, 647.7 cm$^{-1}$. HRMS (m/z): [M$^+$-OH] calcd for C$_{24}$H$_{23}$F$_3$N$_5$O$_4$, 474.1641; found, 474.1650.

EXAMPLE 8

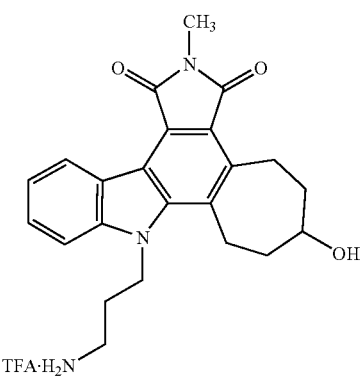

17

Compound 17 was synthesized by Boc deprotection of compound 14 using the procedure of Example 7, as follows:

A 25 mL flask was charged with 14 (34.9 mg, 0.071 mmol) under nitrogen. CH$_2$Cl$_2$ (2 mL) was added to give a yellow suspension. Triisopropylsilane (100 μL, 0.49 mmol) was added followed by TFA (2 mL). The suspension became a dark red solution that was allowed to stir at room temperature under positive nitrogen pressure overnight. The solvent was removed to give a bright yellow solid that was washed with petroleum ether (3×5 mL). The residue was purified by HPLC to give 33.2 mg (93%) of 17.

Data for 17: $^1$H NMR (500 MHz, DMSO-d$_6$, δ): 1.42–1.64 (m, 2H), 1.83–2.12 (m, 4H), 2.22–2.32 (m, 1H), 2.84–3.58 (m, 7H), 3.88–3.96 (m, 1H), 4.61 (t, J=7.6 Hz, 2H), 4.84 (br s, 1H), 7.34–7.38 (m, 1H), 7.60–7.65 (m, 1H), 7.72–7.80 (m, 4H), 9.04 (d, J=7.8 Hz, 1H). IR (KBr): 3423.3, 3060.2, 2939.7, 1781.9, 1751.9, 1686.3, 1438.1, 1376.6, 1330.0, 1290.7, 1203.0, 1173.9, 1037.8, 983.7, 905.0, 837.2, 799.6, 757.3, 741.2, 722.5, 634.7 cm-1. HRMS (m/z): [M$^+$-OH] calcd for C$_{25}$H$_{25}$F$_3$N$_3$O$_4$, 488.1797; found, 488.1792.

EXAMPLE 9

Determination of IC$_{50}$ values for compounds of the invention:

Materials used: Phosphatidyl serine and 1,2 sn-dioleylglycerol were obtained from Serdary Research Laboratories. Protein kinase C, as a mixture of isozymes, was obtained in isolated and purified form from Prof. Daria Mochley-Rosen and Tamar Lion (Stanford University, Department of Molecular Pharmacology).

PKC activity was assayed by measuring $^{32}$Pi transferred from [γ-$^{32}$P]ATP to histone III-S (Sigma). The reaction mixture (100 μL) included 20 mM Tris-HCl (pH 7.5) (30 μL), 10 mM CaCl$_2$ in 20 mM Tris-HCl (10 μL), a sonicated suspension of 2.4 mg/mL phosphatidylserine and 80 μg/mL 1,2-diacylglycerol in 20 mM Tris-HCl (10 μL), a PKC preparation of 4.5 mg/mL total PKC with 5–9 U activity/mL relative to histone III-S (10 μL), a solution of 0.35 mg/mL histone III-S (Sigma) in 20 mM Tris-HCl (10 μL), and a solution of the inhibitor at various concentrations in 20 mM Tris-HCl containing <1% DMSO (10 μL). The reaction was started by the addition of a solution containing 27 μL of 3.75 mM ATP (non-radiolabeled), 100 μL 1.0 M $MgCl_2$, and 1.3 μL of 10 pCi/mL [γ-$^{32}$P]ATP, and 872 μL of 20 mM Tris-HCl (pH 7.5) (20 μL). After 15 min, the reaction was stopped by the addition of 30 μL of 200 mM EDTA and 200 mM ATP (non-radiolabeled). The reaction mixture was adsorbed onto phosphocellulose paper squares (Whatman P81), and allowed to dry for 5 min. The phosphocellulose paper squares were then washed with EtOH (3×1 min). The total protein phosphorylation was quantitated by scintillation counting. Counts per minute were averaged among three trials at each concentration.

The results obtained for various compounds of the invention are as follows:

| | | | Compound: | | | |
|---|---|---|---|---|---|---|
| | 10 | 11 | 12 | 14 | 16 | 17 |
| $IC_{50}$: | >10 μM$^A$ | 3.6 μM | 4.5 μM | >10 μM$^B$ | 0.62 μM | 100 μM$^C$ |

$^A$36% inhibition at 10 μM
$^B$40% inhibition at 10 μM
$^C$49% inhibition at 100 μM

What is claimed is:

1. A compound having the structure of formula (Ia)

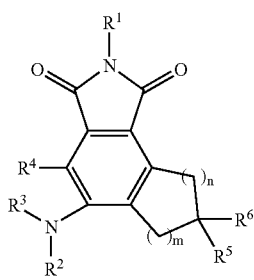

(Ib)

wherein:
m is zero, 1, 2, 3, 4, or 5, and n is zero, 1, 2, 3, 4, or 5, and the sum of m and n is in the range of 2 to 5 inclusive;
$R^1$ is H or lower alkyl;
$R^2$ is H, a heteroatom-protecting group, or -L-$NR^7R^8$ wherein L is a linker containing 1 to 6 spacer atoms, and $R^7$ and $R^8$ are independently selected from hydrogen, nitrogen-protecting groups, $C_1$–$C_{24}$ hydrocarbyl, substituted $C_1$–$C_{24}$ hydrocarbyl, heteroatom-containing $C_1$–$C_{24}$ hydrocarbyl, and substituted heteroatom-containing $C_1$–$C_{24}$ hydrocarbyl;
$R^3$ and $R^4$ are independently selected from hydrogen, $C_1$–$C_{24}$ hydrocarbyl, substituted $C_1$–$C_{24}$ hydrocarbyl, heteroatom-containing $C_1$–$C_{24}$ hydrocarbyl, and substituted heteroatom-containing $C_1$–$C_{24}$ hydrocarbyl, or $R^3$ and $R^4$ taken together form a heterocyclic ring optionally fused to an additional cyclic group;

$R^5$ is a substituent selected from hydrogen, $C_1$–$C_{24}$ hydrocarbyl, substituted $C_1$–$C_{24}$ hydrocarbyl, heteroatom-containing $C_1$–$C_{24}$ hydrocarbyl, or substituted heteroatom-containing $C_1$–$C_{24}$ hydrocarbyl;
$R^6$ is a substituent selected from hydrogen, halo, hydroxyl, sulfhydryl, $C_1$–$C_{24}$ alkoxy, $C_2$–$C_{24}$ alkenyloxy, $C_2$–$C_{24}$ alkynyloxy, $C_5$–$C_{24}$ aryloxy, $C_2$–$C_{24}$ alkylcarbonyl, $C_6$–$C_{24}$ arylcarbonyl, $C_2$–$C_{24}$ alkylcarbonyloxy, $C_6$–$C_{24}$ arylcarbonyloxy, halocarbonyl, $C_2$–$C_{24}$ alkylcarbonato, $C_6$–$C_{24}$ arylcarbonato, carboxy, carboxylato, carbamoyl, mono-($C_1$–$C_{24}$ alkyl)-substituted carbamoyl, di-($C_1$–$C_{24}$ alkyl)-substituted carbamoyl, mono-($C_6$–$C_{24}$ aryl)-substituted carbamoyl, thiocarbamoyl, carbamido, cyano, isocyano, cyanato, isocyanato, isothiocyanato, azido, formyl, thioformyl, amino, mono-($C_1$–$C_{24}$ alkyl)-substituted amino, di-($C_1$–$C_{24}$ alkyl)-substituted amino, mono-($C_5$–$C_{24}$ aryl)-substituted amino, di-($C_5$–$C_{24}$ aryl)-substituted amino, $C_2$–$C_{24}$ alkylamido, $C_6$–$C_{24}$ arylamido, imino, alkylimino, arylimino, nitro, nitroso, sulfo, sulfonato, $C_1$–$C_{24}$ alkylthio, $C_5$–$C_{24}$ arylthio, $C_1$–$C_{24}$ alkylsulfinyl, $C_5$–$C_{24}$ arylsulfinyl, $C_1$–$C_{24}$ alkylsulfonyl, $C_5$–$C_{24}$ arylsulfonyl, phosphono, phosphonato, phosphinato, phosphono, phosphino, $C_1$–$C_{24}$ alkyl, $C_2$–$C_{24}$ alkenyl, $C_2$–$C_{24}$ alkynyl, $C_5$–$C_{24}$ aryl, $C_6$–$C_{24}$ alkaryl, and $C_6$–$C_{24}$ aralkyl, wherein any of the foregoing substituents, if the substituent permits, may be further substituted, or wherein
$R^5$ and $R^6$ taken together form =O, =S, or =$NR^9$ where $R^9$ is selected from hydrogen, $C_1$–$C_{24}$ hydrocarbyl, substituted $C_1$–$C_{24}$ hydrocarbyl, heteroatom-containing $C_1$–$C_{24}$ hydrocarbyl, and substituted heteroatom-containing $C_1$–$C_{24}$ hydrocarbyl,
or a pharmaceutically acceptable, pharmacologically active salt thereof.

2. The compound of claim 1, wherein:
$R^1$ is H
such that the compound has the structure of formula (II)

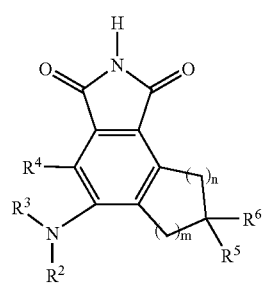

(II)

3. The compound of claim 2, wherein:
$R^2$ is -L-$NR^7R^8$ wherein L is hydrocarbylene containing 2 to 6 spacer atoms, and $R^7$ and $R^8$ are independently selected from hydrogen, nitrogen-protecting groups, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl;
$R^3$ and $R^4$ are independently selected from hydrogen, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl, or $R^3$ and $R^4$ taken together form a five-membered N-heterocyclic ring fused to an additional cyclic group;
$R^5$ is selected from hydrogen and lower alkyl; and $R^6$ is a substituent selected from hydrogen, halo, hydroxyl, sulfhydryl, $C_1$–$C_{12}$ alkoxy, $C_5$–$C_{14}$ aryloxy, $C_2$–$C_{12}$ alkylcarbonyloxy, $C_6$–$C_{14}$ arylcarbonyloxy, halocarbonyl, $C_2$–$C_{12}$ alkylcarbonato, $C_6$–$C_{14}$ arylcarbonato, carboxy, carboxylato, carbamoyl, mono-($C_1$–$C_{12}$ alkyl)-substituted carbamoyl, di-($C_1$–$C_{12}$ alkyl)-substituted carbamoyl, mono-($C_6$–$C_{14}$ aryl)-substituted carbamoyl, thiocarbamoyl, carbamido, cyano, isocyano, formyl, thioformyl, amino, mono-($C_1$–$C_{12}$ alkyl)-substituted amino, di-($C_1$–$C_{12}$ alkyl)-substituted amino, mono-($C_5$–$C_{14}$ aryl)-substituted amino, di-($C_5$–$C_{14}$ aryl)-substituted amino, $C_2$–$C_{14}$ alkylamido, $C_6$–$C_{14}$ arylamido, $C_1$–$C_{12}$ alkylthio, $C_5$–$C_{14}$ arylthio, $C_1$–$C_{12}$ alkyl, $C_2$–$C_{12}$ alkenyl, $C_5$–$C_{14}$ aryl, $C_6$–$C_{16}$ alkar aralkyl, wherein any of the foregoing substituents, if the substituent permits, may be further substituted, or wherein $R^5$ and $R^6$ taken together form =O, =S, or =$NR^9$ where $R^9$ is selected from $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl.

4. The compound of claim 3, wherein:

$R^3$ and $R^4$ are linked to form a pyrrol ring fused to an additional cyclic moiety, such that the compound has the structure of formula (III)

(III)

wherein B is a 5- to 8-membered ring, optionally substituted and/or heteroatom-containing.

5. The compound of claim 4, wherein:

B is a 5- or 6-membered aryl, substituted aryl, heteroaryl, or substituted heteroaryl ring;

the sum of m and n is 2, 3, or 4;

$R^5$ is hydrogen; $R^6$ is selected from hydroxyl, suithydryl, lower alkoxy, and lower alkylthio, or wherein $R^5$ and $R^6$ together form =O;

L is $C_2$–$C_4$ alkylene; and $R^7$ and $R^8$ are independently selected from hydrogen, lower alkyl, and nitrogen-protecting groups.

6. The compound of claim 5, wherein B is an optionally substituted phenyl group, such that the compound has the structure of formula (IV)

(IV)

in which i is an integer in the range of zero to 4, and each R is a nonhydrogen substituent.

7. The compound of claim 6, wherein $R^5$ is hydrogen and $R^6$ is hydroxyl.

8. The compound of claim 7, wherein i is zero.

9. The compound of claim 8, wherein m is 2 and n is 2.

10. The compound of claim 7, wherein L is n-propylene.

11. The compound of claim 6, wherein $R^5$ and $R^6$ taken together form =O.

12. The compound of claim 11, wherein i is zero.

13. The compound of claim 12, wherein m is 2 and n is 2.

14. The compound of claim 11, wherein L is n-propylene.

15. The compound of claim 1, in electronically neutral form.

16. The compound of claim 1, in the form of an acid addition salt.

17. A pharmaceutical composition comprising a pharmaceutically acceptable carrier and a therapeutically effective amount of the compound of claim 1.

18. The composition of claim 17, wherein the therapeutically effective amount is a unit dosage.

19. The composition of claim 17, comprising a sustained release formulation.

* * * * *